(12) United States Patent  
Neel et al.

(10) Patent No.: US 7,955,856 B2
(45) Date of Patent: Jun. 7, 2011

(54) METHOD OF MAKING A DIAGNOSTIC TEST STRIP HAVING A CODING SYSTEM

(75) Inventors: Gary T. Neel, Weston, FL (US); Brent E. Modzelewski, Boca Raton, FL (US); Allan Javier Caban, Lakeworth, FL (US); Adam Mark Will, Boynton Beach, FL (US); Carlos Oti, Plantation, FL (US); Natasha Popovich, Pompano Beach, FL (US); Stephen Davies, Tamarac, FL (US)

(73) Assignee: Nipro Diagnostics, Inc., Ft. Lauderdale, FL (US)

( * ) Notice: Subject to any disclaimer, the term of this patent is extended or adjusted under 35 U.S.C. 154(b) by 634 days.

(21) Appl. No.: 11/594,753

(22) Filed: Nov. 9, 2006

(65) Prior Publication Data

US 2007/0110615 A1 May 17, 2007

Related U.S. Application Data

(63) Continuation-in-part of application No. 11/181,778, filed on Jul. 15, 2005.

(51) Int. Cl.
*G01N 26/18* (2006.01)
(52) U.S. Cl. .............. 436/149; 204/403.14; 204/403.15; 204/413; 204/414; 204/416; 204/434; 204/294
(58) Field of Classification Search ................. 436/149; 204/403.14, 403.15, 413, 414, 416, 434, 204/294

See application file for complete search history.

(56) References Cited

U.S. PATENT DOCUMENTS

| | | |
|---|---|---|
| 3,907,503 A | 9/1975 | Betts et al. |
| 3,964,871 A | 6/1976 | Hochstrasser |
| 4,059,407 A | 11/1977 | Hochstrasser |
| 4,218,421 A | 8/1980 | Mack et al. |
| 4,590,327 A | 5/1986 | Nath et al. |
| 4,615,462 A | 10/1986 | Sacherer et al. |
| 4,627,445 A | 12/1986 | Garcia et al. |
| 4,637,403 A | 1/1987 | Garcia et al. |
| 4,690,801 A | 9/1987 | Anderson |
| 4,717,018 A | 1/1988 | Sacherer et al. |
| 4,757,022 A | 7/1988 | Shults et al. |

(Continued)

FOREIGN PATENT DOCUMENTS

DE  102 22 271 A1  6/2003

(Continued)

OTHER PUBLICATIONS

International Search Report, PCT/US2007/077378, dated Apr. 4, 2008.

(Continued)

*Primary Examiner* — Robert J Hill, Jr.
*Assistant Examiner* — Dwan A Gerido
(74) *Attorney, Agent, or Firm* — Finnegan, Henderson, Farabow, Garrett & Dunner, L.L.P.

(57) ABSTRACT

An auto-calibration system for diagnostic test strips is described for presenting data individually carried on each test strip readable by a diagnostic meter. The carried data may include an embedded code relating to data particular to that individual strip. The data is presented so as to be read by a meter associated with the diagnostic test strip in order to avoid manually inputting the information.

11 Claims, 12 Drawing Sheets

U.S. PATENT DOCUMENTS

| | | | |
|---|---|---|---|
| 4,787,398 A | 11/1988 | Garcia et al. | |
| 4,797,256 A | 1/1989 | Watlington, IV | |
| 4,834,234 A | 5/1989 | Sacherer et al. | |
| 4,871,258 A | 10/1989 | Herpichboehm et al. | |
| 4,876,068 A | 10/1989 | Castaneda | |
| 4,877,580 A | 10/1989 | Aronowitz et al. | |
| 4,894,137 A | 1/1990 | Takizawa et al. | |
| 4,934,556 A | 6/1990 | Kleissendorf | |
| 4,995,402 A | 2/1991 | Smith et al. | |
| 5,087,556 A | 2/1992 | Ertinghausen | |
| 5,096,669 A | 3/1992 | Lauks et al. | |
| 5,104,619 A | 4/1992 | de Castro | |
| 5,149,505 A | 9/1992 | English et al. | |
| 5,279,294 A | 1/1994 | Anderson et al. | |
| 5,281,395 A | 1/1994 | Markart et al. | |
| 5,413,764 A | 5/1995 | Haar | |
| 5,429,804 A | 7/1995 | Sayles | |
| 5,437,999 A | 8/1995 | Diebold et al. | |
| D367,109 S | 2/1996 | Ryner et al. | |
| 5,489,414 A | 2/1996 | Schreiber et al. | |
| 5,494,562 A | 2/1996 | Maley et al. | |
| 5,510,266 A | 4/1996 | Bonner et al. | |
| 5,575,403 A | 11/1996 | Charlton et al. | |
| 5,589,045 A | 12/1996 | Hyodo | |
| 5,630,986 A | 5/1997 | Charlton et al. | |
| 5,645,798 A | 7/1997 | Schreiber et al. | |
| 5,695,623 A | 12/1997 | Michel et al. | |
| 5,709,838 A | 1/1998 | Porter et al. | |
| 5,728,352 A | 3/1998 | Poto et al. | |
| 5,736,103 A | 4/1998 | Pugh | |
| 5,738,244 A | 4/1998 | Charlton et al. | |
| 5,739,039 A * | 4/1998 | Girault et al. | 204/403.14 |
| 5,795,543 A | 8/1998 | Poto et al. | |
| 5,810,199 A | 9/1998 | Charlton et al. | |
| 5,821,399 A | 10/1998 | Zelin | |
| 5,854,074 A | 12/1998 | Charlton et al. | |
| 5,872,713 A | 2/1999 | Douglas et al. | |
| 5,904,898 A | 5/1999 | Markart | |
| 5,951,492 A | 9/1999 | Douglas et al. | |
| 5,989,917 A | 11/1999 | McAleer et al. | |
| 6,036,924 A | 3/2000 | Simons et al. | |
| 6,071,391 A | 6/2000 | Gotoh et al. | |
| 6,099,484 A | 8/2000 | Douglas et al. | |
| 6,106,780 A | 8/2000 | Douglas et al. | |
| 6,159,424 A | 12/2000 | Kauhaniemi et al. | |
| 6,168,957 B1 | 1/2001 | Matzinger et al. | |
| 6,176,119 B1 | 1/2001 | Kintzig | |
| 6,180,063 B1 | 1/2001 | Markart | |
| 6,192,891 B1 | 2/2001 | Gravel et al. | |
| 6,295,506 B1 | 9/2001 | Heinonen et al. | |
| 6,315,738 B1 | 11/2001 | Nishikawa et al. | |
| 6,319,209 B1 | 11/2001 | Kriz | |
| 6,352,514 B1 | 3/2002 | Douglas | |
| 6,379,317 B1 | 4/2002 | Kintzig et al. | |
| 6,540,675 B2 | 4/2003 | Aceti et al. | |
| 6,544,475 B1 | 4/2003 | Douglas et al. | |
| 6,558,897 B2 | 5/2003 | Scheuringer | |
| 6,579,690 B1 | 6/2003 | Bonnecaze et al. | |
| 6,599,406 B1 | 7/2003 | Kawanaka et al. | |
| 6,616,819 B1 | 9/2003 | Liamos et al. | |
| 6,669,908 B2 | 12/2003 | Weyker et al. | |
| 6,682,704 B2 | 1/2004 | Bottwein et al. | |
| D487,594 S | 3/2004 | Alscher et al. | |
| 6,743,635 B2 | 6/2004 | Neel et al. | |
| 6,770,487 B2 | 8/2004 | Crosby | |
| 6,793,802 B2 | 9/2004 | Lee et al. | |
| 6,814,844 B2 | 11/2004 | Bhullar et al. | |
| 6,827,829 B2 * | 12/2004 | Kawanaka et al. | 204/403.02 |
| 6,946,299 B2 | 9/2005 | Neet et al. | |
| 7,073,246 B2 | 7/2006 | Bhullar et al. | |
| 2002/0057993 A1 | 5/2002 | Maisey et al. | |
| 2002/0130042 A1 | 9/2002 | Moerman et al. | |
| 2002/0137059 A1 | 9/2002 | Wu et al. | |
| 2002/0150501 A1 | 10/2002 | Robertson et al. | |
| 2002/0188224 A1 | 12/2002 | Roe et al. | |
| 2003/0031591 A1 | 2/2003 | Whitson et al. | |
| 2003/0031595 A1 | 2/2003 | Kirchhevel et al. | |
| 2003/0032190 A1 | 2/2003 | Brown et al. | |
| 2003/0036200 A1 | 2/2003 | Charlton | |
| 2003/0059350 A1 | 3/2003 | Sacherer | |
| 2003/0106810 A1 | 6/2003 | Douglas et al. | |
| 2003/0109777 A1 | 6/2003 | Kloepfer et al. | |
| 2003/0111357 A1 | 6/2003 | Black | |
| 2003/0129088 A1 | 7/2003 | Lee et al. | |
| 2003/0133847 A1 | 7/2003 | Hagen et al. | |
| 2003/0150724 A1 | 8/2003 | Kawanaka et al. | |
| 2003/0161762 A1 | 8/2003 | Caron et al. | |
| 2003/0175155 A1 | 9/2003 | Charlton | |
| 2003/0178302 A1 * | 9/2003 | Bhullar et al. | 204/403.01 |
| 2003/0185705 A1 | 10/2003 | Otake | |
| 2003/0185708 A1 | 10/2003 | Otake | |
| 2003/0186446 A1 | 10/2003 | Pugh | |
| 2003/0191415 A1 | 10/2003 | Moerman et al. | |
| 2003/0203498 A1 * | 10/2003 | Neel et al. | 436/95 |
| 2003/0207454 A1 | 11/2003 | Eyster et al. | |
| 2003/0208140 A1 | 11/2003 | Pugh | |
| 2003/0211625 A1 | 11/2003 | Cohan et al. | |
| 2003/0212345 A1 | 11/2003 | McAllister et al. | |
| 2003/0219357 A1 | 11/2003 | Douglas et al. | |
| 2003/0223906 A1 | 12/2003 | McAllister et al. | |
| 2004/0007585 A1 | 1/2004 | Griffith et al. | |
| 2004/0026243 A1 | 2/2004 | Davies et al. | |
| 2004/0084307 A1 | 5/2004 | Kim et al. | |
| 2004/0158137 A1 | 8/2004 | Eppstein et al. | |
| 2004/0182703 A1 | 9/2004 | Bell et al. | |
| 2004/0200721 A1 * | 10/2004 | Bhullar et al. | 204/403.01 |
| 2005/0009126 A1 | 1/2005 | Andrews et al. | |
| 2005/0019953 A1 | 1/2005 | Groll | |
| 2005/0023137 A1 | 2/2005 | Bhullar et al. | |
| 2005/0143675 A1 | 6/2005 | Neel et al. | |
| 2005/0279647 A1 | 12/2005 | Beaty | |
| 2006/0189895 A1 | 8/2006 | Neel et al. | |
| 2007/0015286 A1 | 1/2007 | Neel et al. | |
| 2007/0110615 A1 | 5/2007 | Neel et al. | |
| 2008/0020452 A1 | 1/2008 | Popovich et al. | |

FOREIGN PATENT DOCUMENTS

| | | |
|---|---|---|
| EP | 1 288 653 A1 | 3/2003 |
| EP | 1253204 B1 | 5/2006 |
| JP | 10-332626 | 12/1998 |
| JP | 2000-19147 | 1/2000 |
| JP | 2001-311711 | 11/2001 |
| WO | WO 02/00112 | 1/2002 |
| WO | WO 02/088739 A1 | 11/2002 |
| WO | WO 2005/088319 A2 | 9/2005 |
| WO | WO 2007/121121 A2 | 10/2007 |

OTHER PUBLICATIONS

SureFire™ Digital Print Engines—two-page brochure from www.aelora.com (printed Apr. 8, 2004).

VISTASPEC™ Ink Series—two-page brochure from www.aellora.com (printed Apr. 29, 2004).

Office Action dated May 28, 2008, in U.S. Appl. No. 11/181,778, filed Jul. 15, 2005.

Office Action dated Aug. 22, 2008, in U.S. Appl. No. 11/181,778, filed Jul. 15, 2005.

Office Action dated Feb. 24, 2009, in U.S. Appl. No. 11/181,778, filed Jul. 15, 2005.

Office Action dated Jun. 23, 2009, in U.S. Appl. No. 11/181,778, filed Jul. 15, 2005.

Office Action dated Feb. 17, 2009, in U.S. Appl. No. 11/458,298, filed Jul. 18, 2006.

Office Action dated Sep. 1, 2009, in U.S. Appl. No. 11/458,298, filed Jul. 18, 2006.

U.S. Appl. No. 12/115,770, filed May 6, 2008, by Neel et al.

PCT International Search Report, PCT/US2007/072123, dated Nov. 30, 2007.

PCT International Search Report, PCT/US2006/26736, dated May 30, 2008.

(Printed Article) Bohan, M.F.J et al., "Evaluation of Pressures in Flexographic Printing."

(Product Data Sheet) Gwent Electronic Materials Ltd., "Product Data for: -C2000802D2".

(Printed Article) "Roller Coaters," pp. 171-181.
(Product Data Sheet) Creative Materials, "Extremely Conductive Ink."
(Product Data Sheet) Acheson, "Fast Drying, Conductive Graphite Coating."
Office Action dated Dec. 24, 2009, received in U.S. Appl. No. 11/458,298, filed Jul. 18, 2006.

Meier et al., Circuitree 2000, pp. 36-42.
Office Action dated Jan. 12, 2011, received in U.S. Appl. No. 11/458,298, filed Jul. 18, 2006.
Office Action dated Jan. 21, 2011, received in co-pending Australian Patent Application No. 2006270355.

* cited by examiner

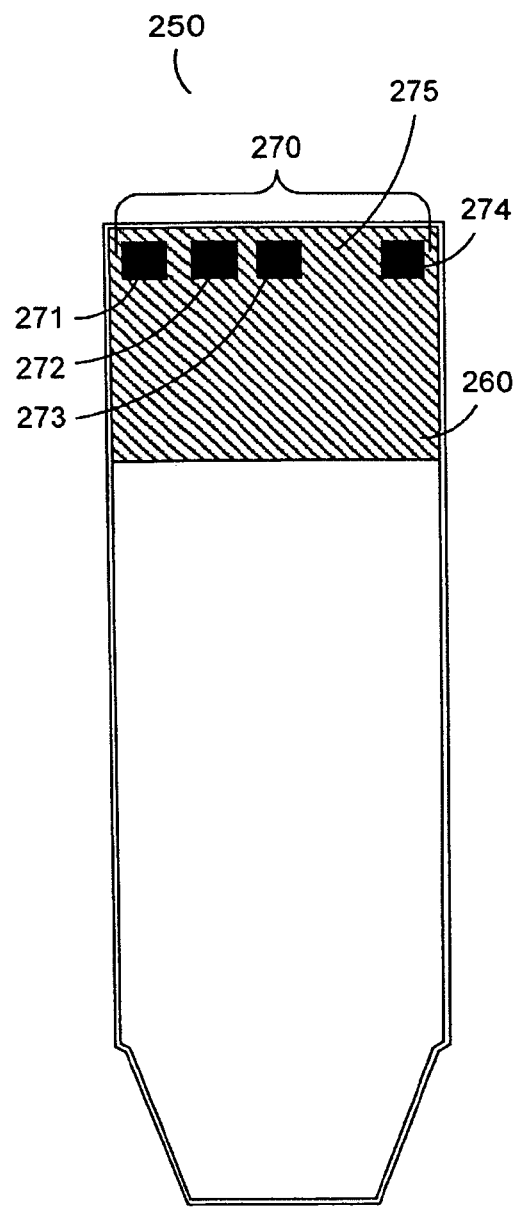
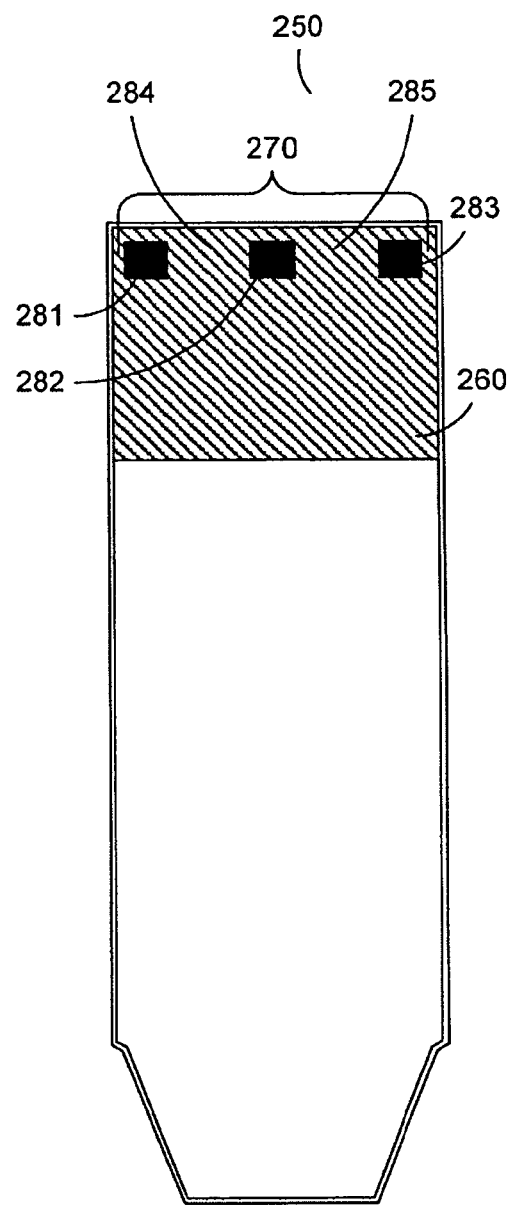
FIG. 14A  FIG. 14B

METHOD OF MAKING A DIAGNOSTIC TEST STRIP HAVING A CODING SYSTEM

CROSS-REFERENCE TO RELATED APPLICATIONS

This application is a continuation in part of co-pending U.S. application Ser. No. 11/181,778, filed Jul. 15, 2005. The content of that application is incorporated herein by reference in its entirety.

DESCRIPTION OF THE INVENTION

1. Field of the Invention

The present invention relates to electrochemical sensors and, more particularly, to systems and methods for electrochemically sensing a particular constituent within a fluid through the use of diagnostic test strips.

2. Background of the Invention

Many industries have a commercial need to monitor the concentration of particular constituents in a fluid. The oil refining industry, wineries, and the dairy industry are examples of industries where fluid testing is routine. In the health care field, people such as diabetics, for example, have a need to monitor a particular constituent within their bodily fluids. A number of systems are available that allow people to test a body fluid, such as, blood, urine, or saliva, to conveniently monitor the level of a particular fluid constituent, such as, for example, cholesterol, proteins, and glucose. Patients suffering from diabetes, a disorder of the pancreas where insufficient insulin production prevents the proper digestion of sugar, have a need to carefully monitor their blood glucose levels on a daily basis. A number of systems that allow people to conveniently monitor their blood glucose levels are available. Such systems typically include a test strip where the user applies a blood sample and a meter that "reads" the test strip to determine the glucose level in the blood sample.

Among the various technologies available for measuring blood glucose levels, electrochemical technologies are particularly desirable because only a very small blood sample may be needed to perform the measurement. In amperometric electrochemical-based systems, the test strip typically includes a sample chamber that contains reagents, such as glucose oxidase and a mediator, and electrodes. When the user applies a blood sample to the sample chamber, the reagents react with the glucose, and the meter applies a voltage to the electrodes to cause a redox reaction. The meter measures the resulting current and calculates the glucose level based on the current. Other systems based on coulometry or voltametry are also known.

Because the test strip includes a biological reagent, every strip manufactured is not reproducible with the exact same sensitivity. Therefore, test strips are manufactured in distinct lots and data particular to that lot is often used as a signal by the meter's microprocessor to assist in accurately performing the meter calculation. The data is used to help accurately correlate the measured current with the actual glucose concentration. For example, the data could represent a numeric code that "signals" the meter's microprocessor to access and utilize a specific set of stored calibration values from an on-board memory device during calculation.

In past systems, the code particular to a specific lot of strips has been input into the meter manually by the user, or connected through some type of memory device (such as a ROM chip) packaged along with test strips from a single manufacturing lot. This step of manual input, or connection by the user, adds to the risk of improperly inputting the wrong code data. Such errors can lead to inaccurate measurements and an improper recording of the patient's history. Past systems have also included bar-code readable information incorporated onto individual strips. Individually imprinting a particular bar-code on each strip adds significant manufacturing costs to the strip production and requires the additional expense of a bar-code reader incorporated within the meter in order to obtain the information.

It should be emphasized that accurate measurements of concentration levels in a body fluid, such as blood, may be critical to the long-term health of many users. As a result, there is a need for a high level of reliability in the meters and test strips used to measure concentration levels in fluids. Thus, it is desirable to have a cost effective auto-calibration system for diagnostic test strips that more reliably and more accurately provides a signaling code for individual test strips.

SUMMARY OF THE INVENTION

Embodiments of the present invention include a test strip, a method of determining a constituent level within a fluid, a method of making a test strip, and a method of making a plurality of test strips that obviate one or more of the limitations and disadvantages of prior devices and methods.

In one embodiment, the invention is directed to a diagnostic test strip. The test strip comprises an electrically insulating base layer, a conductive pattern formed on the base layer providing at least one electrode disposed on the base layer at a proximal region of the strip, electrical strip contacts disposed on the base layer at a distal region of the strip, conductive traces electrically connecting the electrodes to at least some of the electrical strip contacts, and a distinct distal conductive region provided distal to the electrical strip contacts. A reagent layer contacts at least a portion of at least one electrode and an electrically insulating material includes a pattern of apertures. The electrically insulating material is disposed over at least a portion of the distal conductive region such that the apertures expose a pattern of the underlying distal conductive region to at least partially form a distinct pattern readable to identify data particular to the test strip.

In another embodiment the invention is directed to a method of making a test strip. The method comprises providing a sample chamber, providing an electrically insulating base layer, and providing a conductive pattern formed on the base layer including a plurality of electrodes, a plurality of electrical strip contacts, conductive traces electrically connecting the electrodes to at least some of the electrical strip contacts, and a distinct distal conductive region provided distal to the electrical strip contacts, providing an electrically insulating material including a pattern of apertures, and disposing the electrically insulating material over at least a portion of the distal conductive region. The electrically insulating material is disposed such that the apertures expose a pattern of the underlying distal conductive region to at least partially form a distinct pattern readable to identify data particular to the test strip.

In another embodiment the invention is directed to a method of making a plurality of test strips. The method comprises forming a plurality of test strip structures on one sheet. Each of the test strip structures includes a sample chamber, an electrically insulating base layer, and a conductive pattern formed on said sheet. The conductive pattern includes a plurality of electrodes, a plurality of electrical strip contacts, conductive traces electrically connecting the electrodes to at least some of the electrical strip contacts, and a distinct distal conductive region provided distal to the electrical strip contacts. The method further comprises providing an electrically insulating material including a pattern of apertures, disposing the electrically insulating material at least over a portion of the distal conductive region each strip such that the apertures expose a pattern of the underlying distal conductive region on each strip, and separating said test strip structures into said plurality of test strips.

Another embodiment of the invention comprises a method of determining a constituent level within a fluid. The method comprises providing at least one electrically insulating base layer, a conductive pattern formed on the at least one base layer including at least one electrode disposed at a proximal region of the strip, electrical strip contacts disposed at a distal region of the strip, conductive traces electrically connecting the electrodes to at least some of the electrical strip contacts and a distinct distal conductive region provided distal to the electrical strip contacts. A reagent layer contacts at least a portion of at least one electrode. In addition, an electrically insulating material includes a pattern of apertures, the electrically insulating material being disposed over at least a portion of the distal conductive region such that the apertures expose a pattern of the underlying distal conductive region. The method further comprises connecting the distal region of the strip to a constituent level meter such that the electrical strip contacts and the exposed portions of the distal conductive region engage with corresponding meter connector contacts, applying a fluid sample at the reagent layer, taking a measurement using the plurality of electrodes, identifying particular data based on the pattern formed at least in part by the exposed pattern of the distal conductive region, and calculating the fluid constituent concentration based on the value of measured current and the data.

Another embodiment of the invention comprises a method of determining a constituent level within a fluid. The method comprises providing at least one electrically insulating base layer, a conductive pattern formed on the at least one base layer including at least one electrode disposed at a proximal region of the strip, electrical strip contacts disposed at a distal region of the strip, and conductive traces electrically connecting the electrodes to at least some of the electrical strip contacts. A reagent layer contacts at least a portion of at least one electrode. The method further comprises connecting the distal region of the strip to a constituent level meter having a light source and a light detector, such that the electrical strip contacts engage with corresponding meter connector contacts, applying a fluid sample at the reagent layer, taking a measurement using the plurality of electrodes, identifying particular data based on the pattern of apertures by emitting light through the pattern of apertures on one side of the strip and detecting light passing through the pattern of apertures with the light detector on an opposite side of the strip, and calculating the fluid constituent concentration based on the value of measured current and the data.

In another embodiment, the invention is directed to a test strip comprising an electrically insulating base, a conductive pattern formed on the base providing at least one electrode disposed on the base at a proximal region of the strip, electrical strip contacts disposed on the base at a distal region of the strip, conductive traces electrically connecting the electrodes to at least some of the electrical strip contacts, and a distinct distal conductive region provided separate from the electrical strip contacts. A reagent layer contacts at least a portion of at least one electrode and wherein the distal conductive region presents a distinct conductive pattern readable to identify data particular to the test strip.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 14A is a bottom view of an alternative test strip illustrating an alternative configuration for providing a code.

FIG. 14B is a bottom view of a test strip, illustrating an alternative code configuration from that shown in FIG. 14A.

DESCRIPTION OF THE EMBODIMENTS

Figure 1:
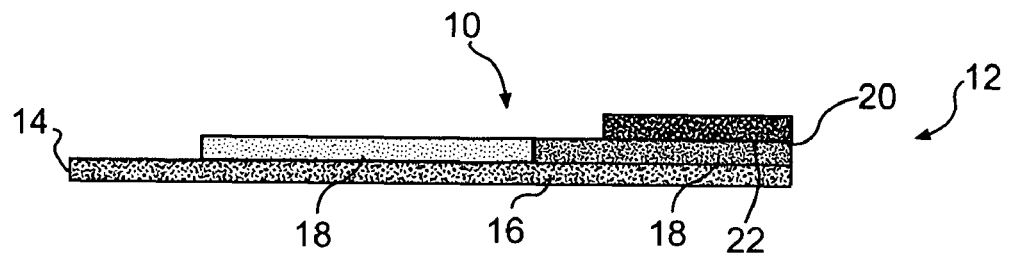
FIG. 1 is a general cross-sectional view of a test strip according to an embodiment of the present invention.

Reference will now be made in detail to the exemplary embodiments of the invention, examples of which are illustrated in the accompanying drawings. Wherever possible, the same reference numbers will be used throughout the drawings to refer to the same or like parts.

According to exemplary embodiments, the invention relates to a system for measuring a body fluid constituent includes a test strip and a meter. An individual test strip may also include an embedded code relating to data associated with a lot of test strips, or data particular to that individual strip. The embedded information presents data readable by the meter signaling the meter's microprocessor to access and utilize a specific set of stored calibration parameters particular to test strips from a manufacturing lot to which the individual strip belongs, or to an individual test strip. The system may also include a check strip that the user may insert into the meter to check that the instrument is electrically calibrated and functioning properly. For purposes of this disclosure, "distal" refers to the portion of a test strip further from the device operator during normal use and "proximal" refers to the portion closer to the device operator during normal use.

The test strip may include a sample chamber for receiving a user's fluid sample, such as, for example, a blood sample. The sample chamber and test strip of the present specification can be formed using materials and methods described in commonly owned U.S. Pat. No. 6,743,635, which is hereby incorporated by reference in its entirety. Accordingly, the sample chamber may include a first opening in the proximal end of the test strip and a second opening for venting the sample chamber. The sample chamber may be dimensioned so as to be able to draw the blood sample in through the first opening, and to hold the blood sample in the sample chamber, by capillary action. The test strip can include a tapered section that is narrowest at the proximal end, or can include other indicia in order to make it easier for the user to locate the first opening and apply the blood sample.

A working electrode and counter electrode can be disposed in the sample chamber optionally along with fill-detect electrodes. A reagent layer is disposed in the sample chamber and preferably contacts at least the working electrode. The reagent layer may include an enzyme, such as glucose oxidase or glucose dehydrogenase, and a mediator, such as potassium ferricyanide or ruthenium hexamine. The test strip has, near its distal end, a first plurality of electrical strip contacts that are electrically connected to the electrodes via conductive traces. In addition, the test strip may also include a second plurality of electrical strip contacts near the distal end of the strip. The second plurality of electrical contacts can be arranged such that they provide, when the strip is inserted into the meter, a distinctly discernable lot code readable by the meter. As noted above, the readable code can be read as a signal to access data, such as calibration coefficients, from an on-board memory unit in the meter related to test strips from that lot, or even information corresponding to individual test strips.

The meter may be battery powered and may stay in a low-power sleep mode when not in use in order to save power. When the test strip is inserted into the meter, the first and second plurality of electrical contacts on the test strip contact corresponding electrical contacts in the meter. The second plurality of electrical contacts may bridge a pair of electrical contacts in the meter, causing a current to flow through the a portion of the second plurality of electrical contacts. The current flow through the second plurality of electrical contacts causes the meter to wake up and enter an active mode. The meter also reads the code information provided by the second plurality and can then identify, for example, the particular test to be performed, or a confirmation of proper operating status. In addition, the meter can also identify the inserted strip as either a test strip or a check strip based on the particular code information. If the meter detects a check strip, it performs a check strip sequence. If the meter detects a test strip, it performs a test strip sequence.

In the test strip sequence, the meter validates the working electrode, counter electrode, and, if included, the fill-detect electrodes, by confirming that there are no low-impedance paths between any of these electrodes. If the electrodes are valid, the meter indicates to the user that sample may be applied to the test strip. The meter then applies a drop-detect voltage between the working and counter electrodes and detects a fluid sample, for example, a blood sample, by detecting a current flow between the working and counter electrodes (i.e., a current flow through the blood sample as it bridges the working and counter electrodes). To detect that an adequate sample is present in the sample chamber and that the blood sample has traversed the reagent layer and mixed with the chemical constituents in the reagent layer, the meter may apply a fill-detect voltage between the fill-detect electrodes and measures any resulting current flowing between the fill-detect electrodes. If this resulting current reaches a sufficient level within a predetermined period of time, the meter indicates to the user that adequate sample is present and has mixed with the reagent layer.

The meter can be programmed to wait for a predetermined period of time after initially detecting the blood sample, to allow the blood sample to react with the reagent layer or can immediately begin taking readings in sequence. During a fluid measurement period, the meter applies an assay voltage between the working and counter electrodes and takes one or more measurements of the resulting current flowing between the working and counter electrodes. The assay voltage is near the redox potential of the mediator in the reagent layer, and the resulting current is related to the concentration of the particular constituent measured, such as, for example, the glucose level in a blood sample.

In one example, the reagent layer may react with glucose in the blood sample in order to determine the particular glucose concentration. In one example, glucose oxidase is used in the reagent layer. The recitation of glucose oxidase is intended as an example only and other materials can be used without departing from the scope of the invention. Other possible enzymes include, but are not limited to, glucose dehydrogenase. During a sample test, the glucose oxidase initiates a reaction that oxidizes the glucose to gluconic acid and reduces the ferricyanide to ferrocyanide. When an appropriate voltage is applied to a working electrode, relative to a counter electrode, the ferrocyanide is oxidized to ferricyanide, thereby generating a current that is related to the glucose concentration in the blood sample. The meter then calculates the glucose level based on the measured current and on calibration data that the meter has been signaled to access by the code data read from the second plurality of electrical contacts associated with the test strip. The meter then displays the calculated glucose level to the user. Each of the above-described components and their interconnection will now be described.

FIG. 1 illustrates a general cross-sectional view of an embodiment of a test strip 10. Test strip 10 includes a proximal connecting end 12, a distal end 14, and is formed with a base layer 16 extending along the entire length of test strip 10. Base layer 16 is preferably composed of an electrically insulating material and has a thickness sufficient to provide structural support to test strip 10. For purposes of this application, an insulating material (e.g. an insulating layer, coating, ink, or substrate etc.) comprises any material in which electrons or ions cannot be moved easily, hence preventing the flow of electric current. Accordingly, an element can be said to be insulated when it is separated from other conducting surfaces by a dielectric substance or air space permanently offering a high resistance to the passage of current and to disruptive discharge through the substance or space. By contrast, for purposes of this application, a resistive element, is one that introduces an increased level of impedance into a circuit that reduces (but does not necessarily prevent) the flow of electric current. Base layer 16, for example, may be polyester that is about 0.010 inches think, although other sizes my be used depending on the particular application and manufacturing method. Disposed on base layer 16 is a conductive pattern (not shown).

The conductive pattern includes a plurality of electrodes disposed on base layer 16 near proximal end 12, a plurality of electrical strip contacts disposed on base layer 16 near distal end 14, and a plurality of conductive traces electrically connecting the electrodes to the plurality of electrical strip contacts. For purposes of this application, the noun "contact" denotes an area intended for mechanical engagement with another corresponding "contact" irrespective of whether an electric circuit is completed, or passes through the particular area.

In one embodiment, the plurality of electrodes may include a working electrode, a counter electrode, and fill-detect electrodes. The conductive pattern may be applied by applying a conductive material onto base layer 16. The conductive pattern can be applied to the top side of the strip, the bottom side of the strip, or a combination of both. The electrode material may be provided by thin film vacuum sputtering of a conductive material (e.g. Gold) and a semiconductive material (e.g. Indium Zinc Oxide) onto the base layer 16. The resulting electrode layer can then by further patterned according to the specific application by forming particular conductive regions/pathways through a laser ablation process. Alternative materials and methods for providing a conductive pattern in addition to screen printing can be employed without departing from the scope of the invention.

A dielectric insulating layer 18 can be formed over the conductive pattern along a portion of the test strip between the measuring electrodes and the plurality of electrical strip contacts in order to prevent scratching, and other damage, to the electrical connection. As seen in FIG. 1, the proximal end 12 of test strip 10 includes a sample receiving location, such as a sample chamber 20 configured to receive a patient's fluid sample, as described above. The sample chamber 20 may be formed in part through a slot in the dielectric insulating layer formed between a cover 22 and the underlying measuring electrodes formed on the base layer 16. The relative position of the measuring electrodes and the electrical strip contacts form a proximal electrode region 24 at one end of strip 10 and a distal strip contact region 26 at the other end.

Figure 2:
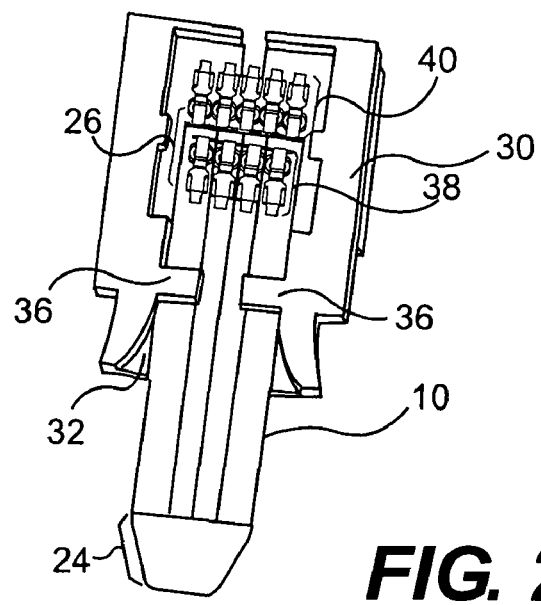
FIG. 2 is a top perspective view of a test strip inserted within a meter strip connector according to an embodiment of the present invention.

Referring to FIG. 2, a top perspective view of a test strip 10 inserted within a meter connector 30 is illustrated. As seen in FIG. 2, the strip 10 includes a proximal electrode region 24, which contains the sample chamber and measuring electrodes described above. The proximal electrode region 24 may be formed to have a particular shape in order to distinguish to the user, the end receiving a fluid sample from distal strip contact region 26. The meter connector 30 includes channel 32 extending out to a flared opening for receiving the test strip 10. The connector 30 may further include tangs 36 extending a predetermined height above the base of channel 32. The predetermined height of tangs 36 is selected to limit the extent, such as through a corresponding raised layer of test strip 10, to which a test strip 10 can be inserted into channel 32.

Figure 3:
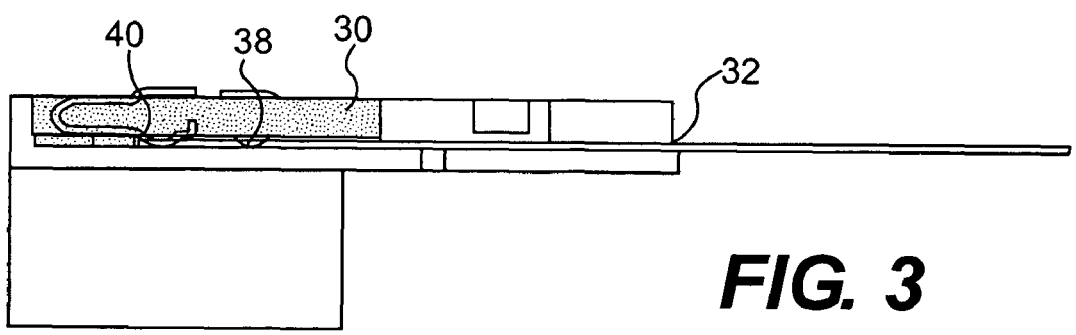
FIG. 3 is a general cross-sectional view of a test strip inserted within a meter strip connector according to an embodiment of the present invention.

The connector 30 further includes a first plurality of connector contacts 38, disposed closer to the proximal end of the connector 30, and a second plurality of connector contacts 40 disposed closer to the distal end of the connector 30. As illustrated, the test strip 10 is inserted into the flared opening with the distal strip contact region 26 extending first through the connector channel 32. With reference to FIG. 3, a general cross-sectional view of a test strip inserted within a meter strip connector 30 is illustrated. The channel 32 depicts a proximal row of connectors comprising a first plurality of connector contacts 38. In addition, the channel 32 houses a distal row of connectors comprising a second plurality of connector contacts 40. The connector contacts 38 and 40 make contact with distinct portions of the distal strip contact region 26, as will be described more fully below.

Figure 4A:
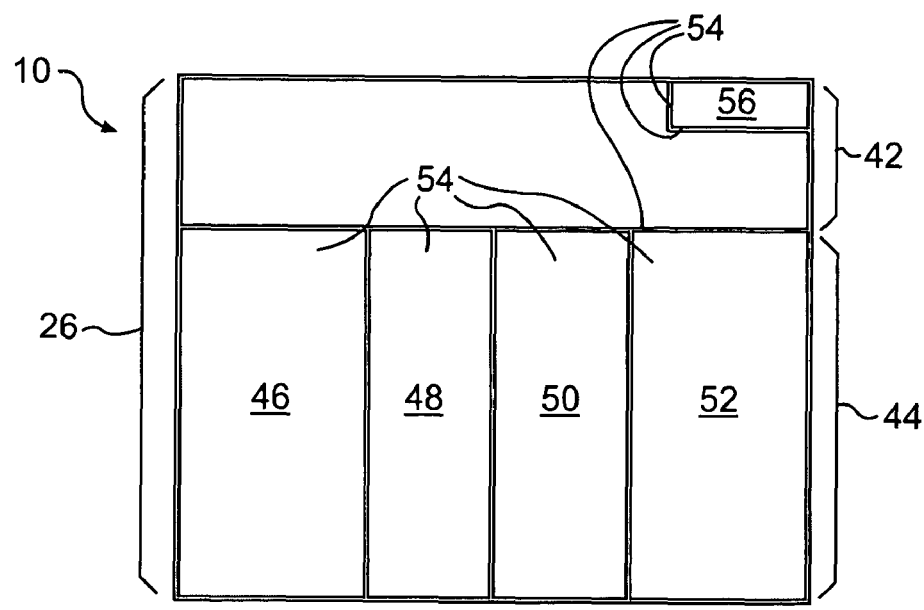
FIG. 4A is a top view of a distal portion of a test strip illustrating breaks dividing particular regions of the test strip connecting end according to an embodiment of the present invention.

FIG. 4A is a top view of a distal portion of a test strip 10 illustrating the distal strip contact region 26. The conductive pattern formed on base layer 16 extends along strip 10 to include the distal strip contact region 26. As illustrated in FIG. 4A, distal strip contact region 26 is divided to form two distinct conductive regions, 42 and 44 respectively. Conductive region 44 is divided into four columns forming a first plurality of electrical strip contacts, labeled 46, 48, 50, and 52 respectively. The first plurality of electrical strip contacts are electrically connected to the plurality of measuring electrodes at the distal end of the test strip 10 as explained above. It should be understood that the four contacts 46-52 are merely exemplary, and the system could include fewer or more electrical strip contacts corresponding to the number of measuring electrodes included in the system.

The first plurality of electrical strip contacts 46-52 are divided, for example, through breaks 54 formed through the underlying conductive pattern in the test strip 10. These breaks could be formed in the conductive pattern during printing, through a scribe process, laser ablated, or through a chemical/photo-etching type process. In addition, other processes of forming conductive breaks by removing a conductor in the test strip 10 may be used as would be apparent to one having ordinary skill in the art. An additional break 54 divides conductive region 44 from conductive region 42 within distal strip contact region 26, and a further break 54 separates the upper right-hand portion of distal strip contact region 26 to form a notch region 56, as will be described more fully in detail below.

Figure 4B:
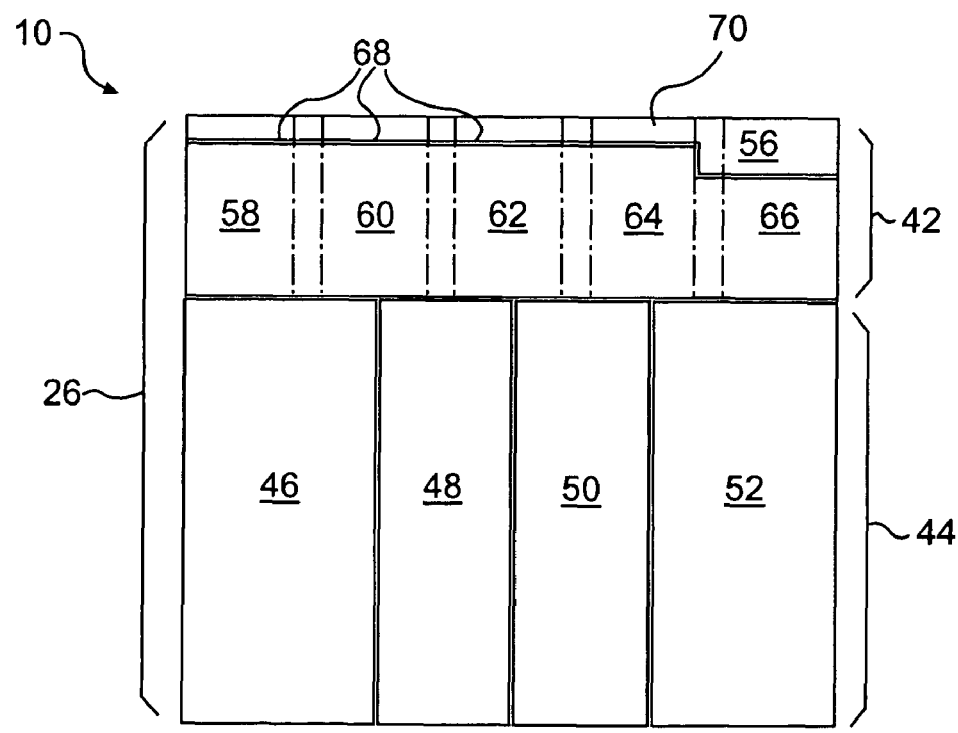
FIG. 4B is a top view of a distal portion of a test strip illustrating conductive regions forming electrical contacts according to an embodiment of the present invention according to an embodiment of the present invention.

FIG. 4B illustrates an additional view of the distal strip contact region 26. In FIG. 4B, conductive region 42, described above with regard to FIG. 4A, is divided into five distinct regions outlining a second plurality of electrical strip contacts forming contacting pads 58, 60, 62, 64, and 66 respectively. The second plurality of electrical strip contacts forming contacting pads 58, 60, 62, 64, and 66, can be divided through the same process used to divide the first plurality of electrical strip contacts, 46, 48, 50, and 52, described above. As noted above, the conductive pattern on base layer 16, which at least in part forms the electrical strip contacts, can be applied to the top side of the strip, the bottom side of the strip, or a combination of both. The contacting pads 58, 60, 62, 64, and 66 are configured to be operatively connected to the second plurality of connector contacts 40 within meter connector 30. Through this operative connection, the meter is presented with, and reads from the contacting pads, a particular code representing information signaling the meter to access data related to the underlying test strip 10. In addition, FIG. 4B depicts a further pattern of breaks 68, isolating an outermost distal connecting end 70 of the distal strip contact region 26.

Figure 4C:
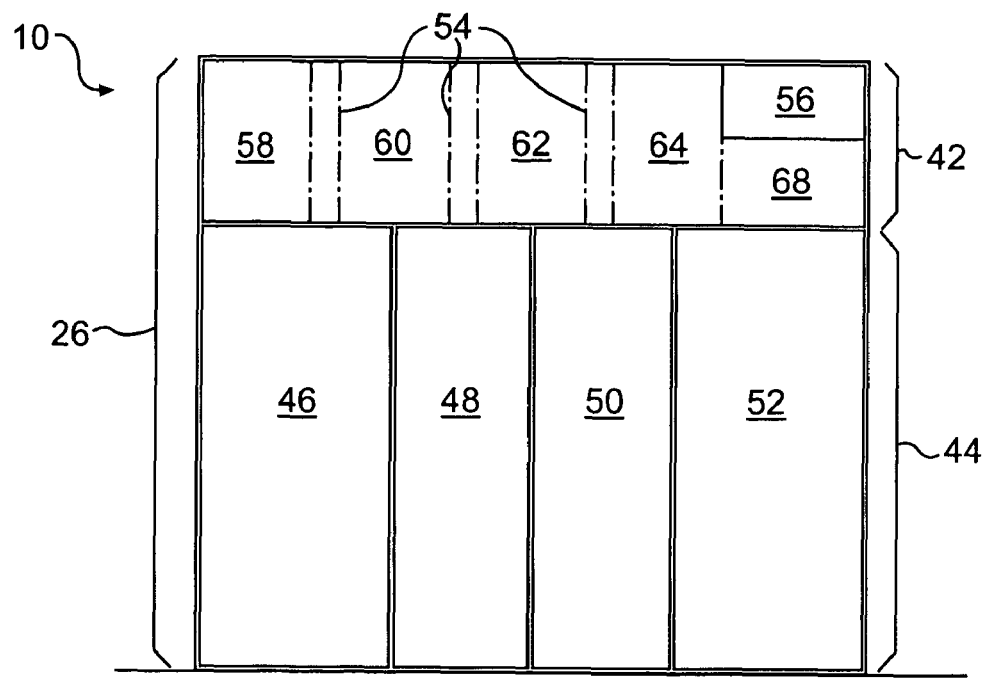
FIG. 4C is a top view of a distal portion of a test strip illustrating a particular arrangement for a plurality of electrical contacts according to an embodiment of the present invention.

FIG. 4C illustrates an additional view of the distal strip contact region 26. In FIG. 4C, the distal strip contact region 26 is depicted to include the first plurality of electrical strip contacts 46-52, the second plurality of electrical strip contacts forming contacting pads 58, 60, 62, 64, and 66, and the separated notch region 56. As noted, the above described conductive regions can all be formed as a result of breaks 54 within the underlying conductive pattern of test strip 10.

Figure 4D:
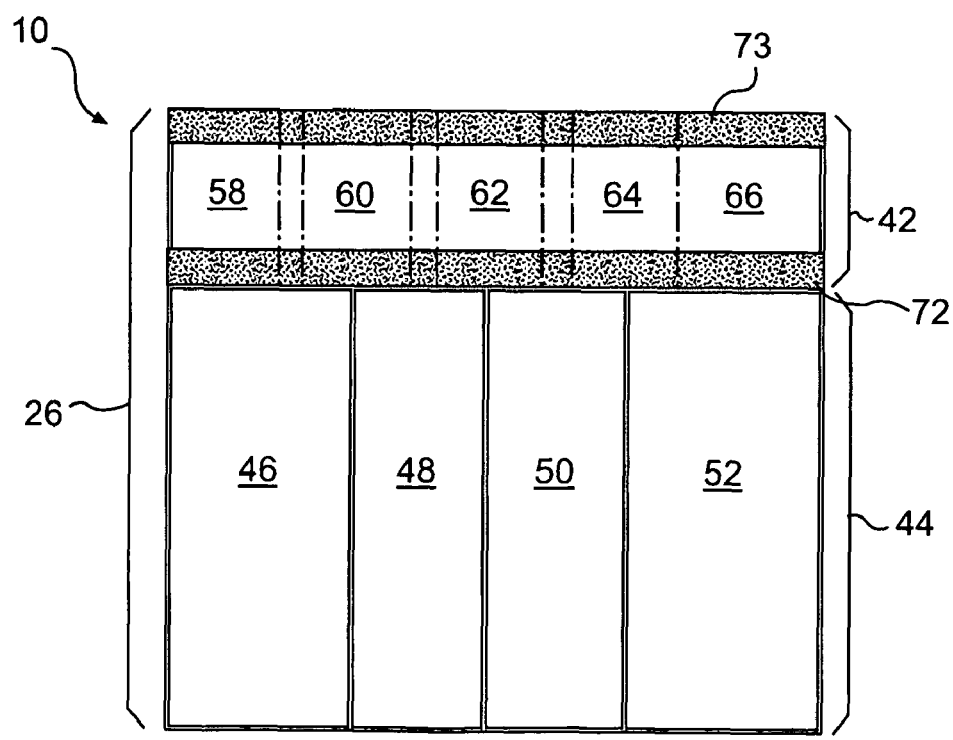
FIG. 4D is a top view of a distal portion of a test strip illustrating multiple insulators covering particular regions of the test strip connecting end according to an embodiment of the present invention.

FIG. 4D illustrates additional features of the distal strip contact region 26. A strip of non-conductive insulating ink 72 can provide further separation between conductive region 44 and conductive region 42 within distal strip contact region 26. The borders between the two regions can be printed with the insulating ink 72 in order to maintain distinct areas of conductivity (bordered by a distinct area of insulation) and to prevent scratching by meter connector contacts during the strip insertion process, which can adversely affect the desired conductivity of one of the strip contacts. The non-conductive insulating ink 72 can be administered, for example, through a screen or ink jet printing process. Such printing of a dielectric insulation coating is advantageous in that it can be applied later on in the strip manufacturing process and in an easily programmable/reproducible pattern. The additional step of adding such an insulating coating can be less expensive and time consuming than methods requiring substrate ablation in some form. For example, ablating a substrate surface through a laser or chemical ablation process involves a time consuming process of precisely removing a particular pattern of preexisting material.

FIG. 4D illustrates that test strip 10 may include another strip of non-conductive insulating ink 73 formed at the distal end of the test strip 10. The strip of non-conductive insulating ink 73 provides a non-conductive region at the distal end of the strip 10. The strip 73 thereby prevents any meter connector contacts from creating an active conductive connection with any portion of contacting pads 58, 60, 62, 64, and 66 before the strip is fully inserted into the meter. Accordingly, strip 73 provides an additional feature for assuring a proper connection between the test strip 10 and the corresponding meter.

Figure 5:
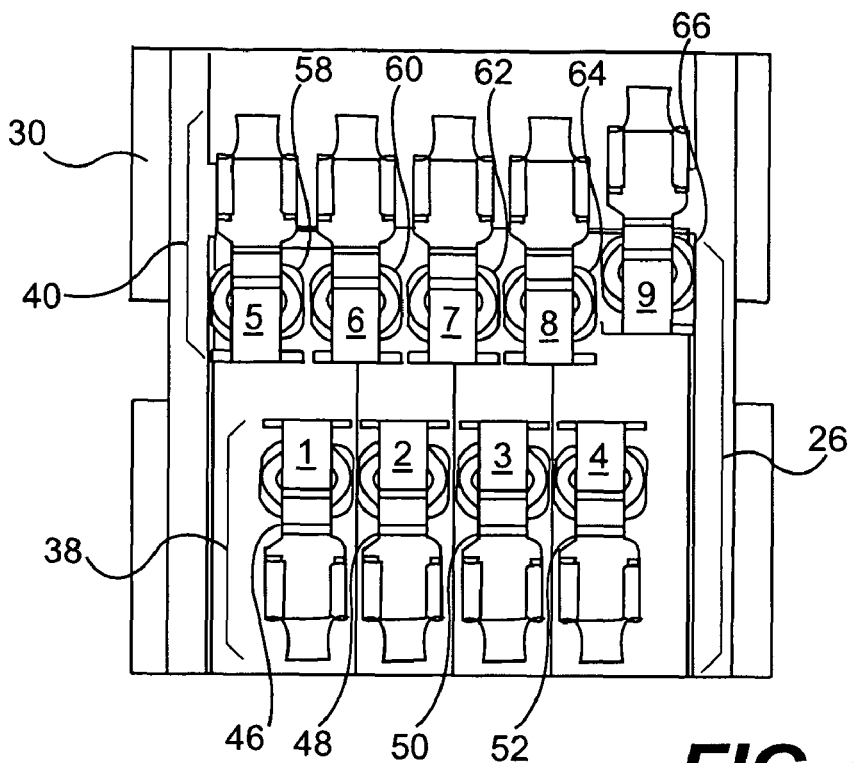
FIG. 5 is an expanded top view of a distal portion of a test strip inserted within a meter strip connector according to an embodiment of the present invention.

Referring to FIG. 5, meter strip connector 30 is illustrated receiving a distal strip contact region 26 of test strip 10. FIG. 5 depicts a first plurality of connector contacts 38, labeled 1-4 respectively, and a second plurality of connector contacts 40, labeled 5-9. The connector contacts 38 and 40 make contact with distinct portions of the distal strip contact region 26. In particular, upon proper insertion of the test strip 10 into connector 30, the electrical strip contacts 46-52, which form the first plurality of electrical strip contacts, are respectively electrically connected to the connector contacts 1-4, which form the first plurality of connector contacts 38. Similarly, the contacting pads 58, 60, 62, 64, and 66, which form the second plurality of electrical strip contacts, are respectively electrically connected to the connector contacts 5-9, which form the second plurality of connector contacts 40.

As seen in FIG. 5, the first plurality of connector contacts 38 are laterally staggered or offset, relative to the second plurality of connector contacts 40. Although the first and second plurality are illustrated as being in distinct rows and offset from each other, they need not be in distinct rows and can instead be offset in an additional manner, such as, for example, in distinct groups. Accordingly, as a test strip 10 is inserted into meter connector 30, the conductive signal provided by contacting pads 58-66 is unhindered by any scratches or scuffs that would otherwise result from first sliding contacting pads 58-66 under connector contacts 1-4 in order to reach their destination connection at connector contacts 5-9. Therefore, the staggered arrangement of connector contacts 38 relative to connector contacts 40 provides a more reliable connection. In addition, the application of strip 72 of non-conductive insulating ink (FIG. 4D) also assists in preventing the conductive coating from one of contacting pads 58-66 from being scratched and "plowed" away by the friction and interaction from the meter connector contacts 38. Accordingly, strip 72 of non-conductive insulating ink provides increased reliability of connector and contact conduction.

In one embodiment, the connection between contacting pad 66 and connector contact 9 establishes a common connection to ground (or a voltage source where the polarity is reversed), thereby completing an electric circuit, which includes the meter and at least a portion of conductive region 42. The completion of this circuit can perform a meter wake-up function, providing a signal to the meter to power up from low-power sleep mode. Therefore, as illustrated in FIG. 5, the connector contact 9 may be positioned proximally relative to the remaining contacts 5-8, in order to ensure that connectors 5-8 are in proper connecting position prior to the final closing/wake-up of the circuit through the connection of contacting pad 66 and connector contact 9. Furthermore, because the a non-conductive insulating ink strip 73 (See FIG. 4D) can be formed at the distal end of the test strip 10 and also because a conducting substance can be removed from notch region 56 (See FIG. 4C), premature wake-up of the meter will be prevented.

In other words, during distal movement of test strip 10 within the connector channel 32, the common connection will not be established at the point connector contact 9 engages the extreme distal edge of test strip 10. Instead, common connection will be established only when the connector contact passes notch 56, and ink strip 73 if applied, and engages a conductive portion of contacting pad 66. Accordingly, the combination of a proximally positioned connector contact 9 and a non-conductive notch region 56 provides a more reliable connection between strip 10 and the meter.

As noted above, the contacting pads 58, 60, 62, 64, and 66 are configured to be operatively connected to the second plurality of connector contacts 40 within meter connector 30. Through this operative connection, the meter is presented with, and reads from the contacting pads, a particular code signaling the meter to access information related to a particular underlying test strip 10. The coded information may signal the meter to access data including, but not limited to, parameters indicating the particular test to be performed, parameters indicating connection to a test probe, parameters indicating connection to a check strip, calibration coefficients, temperature correction coefficients, ph level correction coefficients, hematocrit correction data, and data for recognizing a particular test strip brand.

Figure 6:
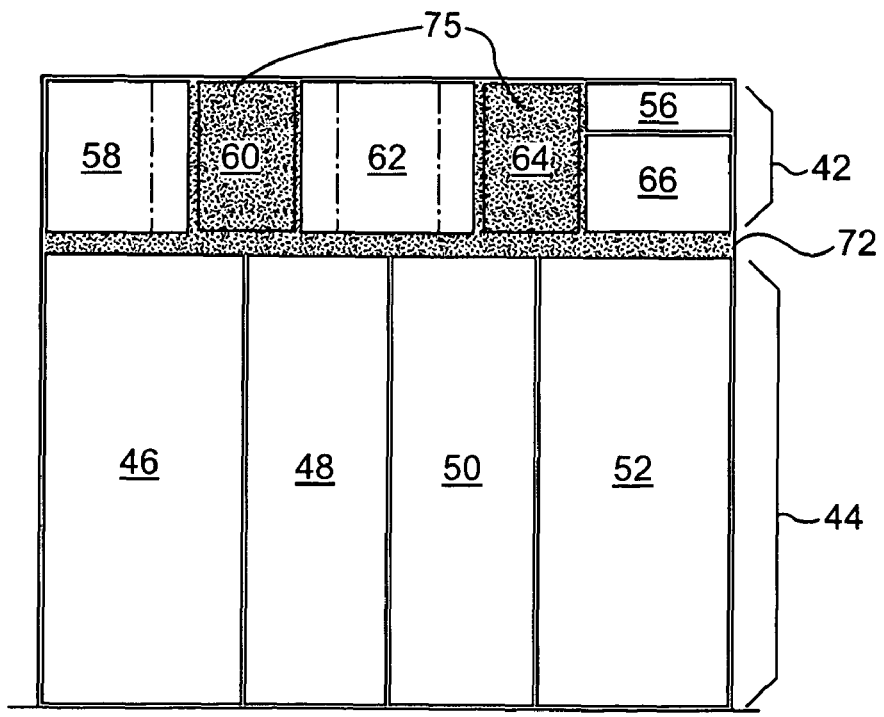
FIG. 6 is a top view of a distal portion of a test strip illustrating a plurality of electrical contacts forming a code according to an embodiment of the present invention.

One such code is illustrated in FIG. 6, where conductive contacting pads 60 and 64 are overprinted with an electrical insulting material, such as, for example, a non-conductive (insulating) ink layer 75. A non-conductive ink layer 75 significantly increases the impedance (and may even preventing the flow of electric current therealong) between the corresponding connector contacts (in this example, connector contacts 6 and 8) and the underlying strip portion at various predetermined contacting pads within the conductive region 42 of distal strip contact region 26. Just as described above, with regard to FIG. 4D, the use of non-conductive insulating ink 75 is particularly advantageous relative to other methods of altering the conductivity of a strip portion.

An exemplary insulating material includes, but is not limited to, VISTASPEC HB Black available from Aellora™ Digital of Keene, N.H. The VISTASPEC HB Black material is a hybrid UV-curable black-pigmented ink for use in elevated temperature piezo drop-on-demand ink jet arrays. This VISTASPEC ink is jetted at an elevated temperature, rapidly sets upon contact with the underlying substrate, and is then cured by UV radiation. The ink's properties include electrical insulation, resistance to abrasion from a meter's contacts, enhanced adhesion to an underlying conductive material, and beneficial visco-elastic characteristics. The material's visco-elastic characteristics minimize ink spreading on the underlying substrate. Furthermore, these visco-elastic characteristics enable this ink to be utilized with high print resolution piezo technology that enables accurate and precise patterning of the VISTASPEC ink onto the conductive electrode substrate. In addition, the visco-elastic characteristics of the VISTASPEC ink enables a sample as small as about an 80 picoliter drop to remain pinned at the location where it makes contact with the underlying substrate, thereby enabling precise pad sizes, positional accuracy, and precision of up to less than about 0.005 inches. As an example, printing of the insulating material can be accomplished through the use of a SureFire Model PE-600-10 single pass piezo drop-on-demand ink jet print engine, also available from Aellora™ Digital of Keene, N.H. As non-limiting examples, the above described ink jet print engine can utilize Nova and Galaxy model print heads available from Spectra Inc. of Lebanon, N.H.

Systems requiring the ablation of a substrate surface through a laser or chemical ablation process involves the time consuming process of precisely removing a particular pattern of preexisting material. Because coding of the strip occurs later in the assembly process than the ablation step, adding a non-conductive ink layer 75 to the contacting pads eliminates the tolerance issues that would result from reintroducing strips into a larger ablation process for coding. Such printing of a dielectric insulation coating is advantageous in that it can be applied later on in the strip manufacturing process and in an easily programmable/reproducible pattern. As a non-limiting example, the method of providing layer 75 to the underlying substrate can include the use of at least one registration datum along the underlying strip to insure accurate formation of the layer 75 according to a particular desired pattern. For example, datums can be provided orthogonally (e.g. longitudinally and laterally) along a substrate where that can be mechanically or optically referenced by a printing apparatus to facilitate the formation of an accurate and reproducible pattern. Depending on the arrangement of the electrical strip contacts, the discrete portions of electrical insulating material forming each layer 75 can be applied to the top side of the strip, the bottom side of the strip, or a combination of both.

Upon connection of the contacting pads 58, 60, 62, 64, and 66 in FIG. 6 to the corresponding connector contacts 40, the meter will read a particular code based on the number, and pattern, of contacting pads overprinted with a non-conductive ink layer 75. In other words, the use of non-conductive ink layer 75, provides a switching network to be read by the meter. When an insulator is printed over one of the conductive surfaces of contacting pads 58, 60, 62, 64, and 66, it prevents the flow of electric current therealong and alters the conductive path between the contacting pad and connector contact (e.g. where no current flows). When no insulator is printed over the conductor current flow is relatively unimpeded (a low impedance path).

Upon reading a particular code, an internal memory within the meter can access, through a stored microprocessor algorithm, specific calibration information (such as, for example, calibration coefficients) relating to the particular test strip. The meter can read the code through either an analog or digital method. In the analog mode, a preset resistive ladder is interconnected within the meter to the second plurality of connector contacts 40 (labeled 5-9 in FIG. 5) such that permutations of printed non-conductive ink can be correlated to a distinct lot code using a voltage drop, resistance, or current measurement. The analog method also can be simultaneously used as the auto-on/wake-up feature as long as each code has at least one pad free of non-conductive ink that can make a low impedance connection to wake the meter up by closing an open circuit. The analog voltage, resistance, or current level could be used to signal the meter to access any of the data referenced above particular to the underlying test strip.

Figure 7:
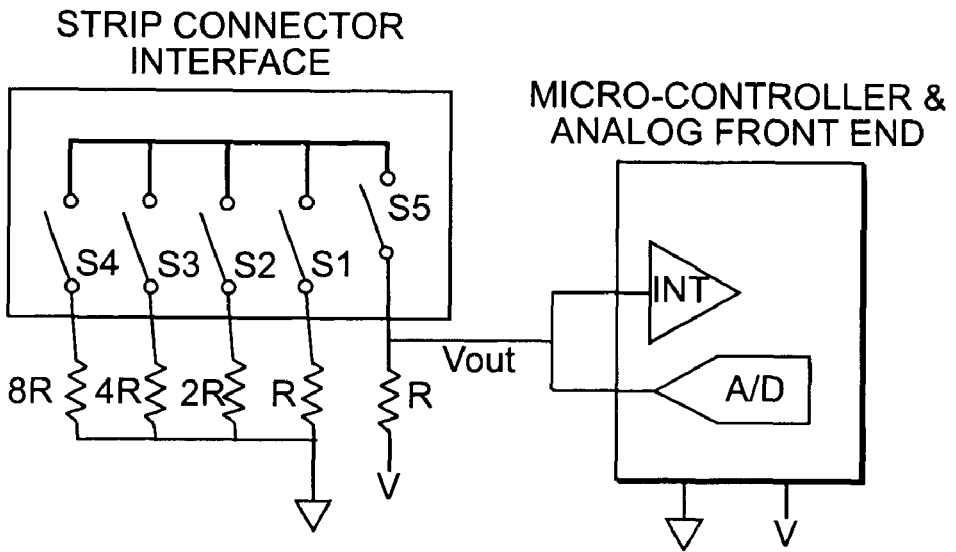
FIG. 7 is a simplified schematic diagram of the electrical connections between a meter and a plurality of electrical contacts of a test strip according to an embodiment of the invention according to an embodiment of the present invention.

FIG. 7 depicts a schematic diagram of the electrical connections between a meter and contacting pads 58, 60, 62, 64, and 66 of a test strip according to an embodiment of the invention. Switch S5 of FIG. 7 provides the connection to a single voltage source V. Accordingly, switch S5, represents the required connection of contacting pad 66 and connector contact 9 in the analog code reading process. Switches S4-S1 schematically represent the connection between connector contacts 5-8 and contacting pads 58-64 of FIG. 5, respectively. When a non-conductive ink layer 75 is provided over one of the contacting pads 58, 60, 62, and 64, the corresponding switch, S4, S3, S2, or S1, will prevent the flow of electric current therealong upon physical engagement with a corresponding connector contacts 5-8. Accordingly, a particular code will correspond to a particular switching configuration, in the switch network of FIG. 7.

As further seen in FIG. 7, each of switches S4-S1 close to add a distinct value of additional impedance to the closed circuit, by bridging the connection to a particular resistor. Therefore, through the application of Ohm's and Kirchhoff's laws, a circuit measurement at $V_{out}$ will provide distinct values based on the particular code presented by test strip 10. In an alternative embodiment, the direction of current flow can be reversed, if desired, by connecting switch S5 to common ground and instead connecting the resistor R to the single voltage source.

Figure 8:
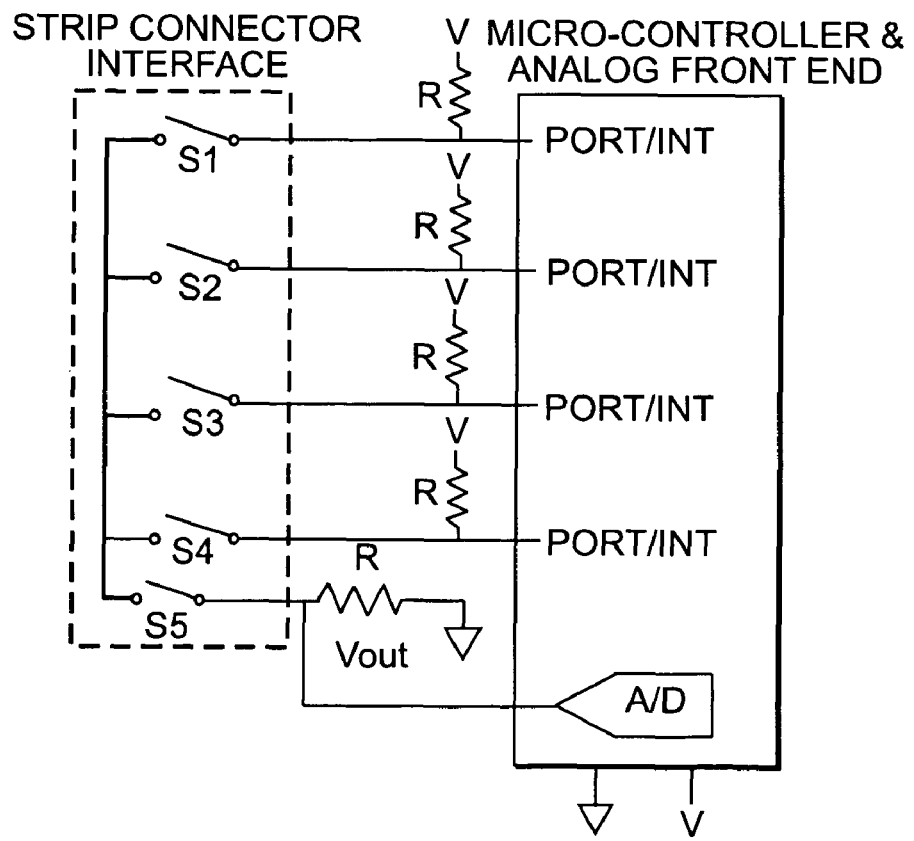
FIG. 8 is an alternative simplified schematic diagram of the electrical connections between a meter and a plurality of electrical contacts of a test strip according to an embodiment of the invention.

In the digital mode, as schematically represented in FIG. 8, each contacting pad 58-66, would be read as an individual input, unlike the single input used by the analog method. For the digital method to be simultaneously used as an auto-on/wake-up feature, the inputs would need to be wire-orred together or connected to an interrupt controller of a microcontroller. Each code must have at least one pad free of non-conductive ink 75 such that a low impedance connection can be made to wake-up the meter's micro-controller.

Non-conductive ink 75 with levels of high and low impedance produce a binary code yielding a code index based on the number of pads (P) implemented, where the number of codes is $N=2^P$. It is possible, however, for a code to comprise an arrangement where none of the electrical strip contacts are covered with electrical insulating material (a code will all logical "1"s, i.e. all conductors). The number of codes possible when integrated with an auto-on/wake-up feature, however, is reduced to $N=2^P-1$. In a system having an auto-on/wake-up feature, a code with all zeros (all insulators) is not an active code as it will not wake up the meter.

When a strip 10 is inserted into the meter connector 30, one contact is closed and wakes up the meter by pulling the microcontroller's interrupt either high or low. The meter will then check the voltage out ($V_{out}$) to determine the test type and then read the code bits (S1,S2,S3,S4) to determine the code value. The code value selected can, for example, be associated with a stored set of coefficients in the meter's memory for use in a glucose mapping algorithm that is particularly correlated to the reagent applied to the measuring electrode region. This code can also be associated with other types of strip parameter information, such as those referenced above. It could also select different meter configuration options as well. The voltage drop across the series resistor R at Vout in FIG. 8 can be sensed, to determine if code vales are within a predetermined range for use as a confirmation signal. This can also be used to determine strip identification (check strip, manufacturing probe, and different test type).

In addition to providing either a high or low impedance level (through the application or absence of an insulating layer of non-conductive ink 75 over one of the contacting pads) a particular resistive element may be applied over a particular contacting pad. The resistive element introduces an increased level of impedance into a circuit that reduces (but does not necessarily prevent) the flow of electric current. Accordingly, the use of a specific resistive element over a particular contacting pad provides an intermediate level of resistance directly on the contacting pad of the test strip. When this intermediate level of resistance is connected to the meter through engagement with a corresponding meter connector contact, the meter can detect this "intermediate" level (e.g. through a circuit measurement of voltage drop by applying Ohm's and Kirchhoff's laws).

The detection of such an intermediate level can alert the meter's processor to access an entire new set of code data relating to the particular test strip. In other words, providing a resistive element coating can be used to expand the number of codes available with a set number of contacting pads. For example, a strip may be formed with a particular code through a particular pattern of non-conducting insulating ink 75. When one of the conducting contacting pads is formed to include a particular resistive element, that same code represented by the pattern of non-conducting ink 75 now can be read by the meter to access an entirely different set of data. As an example, the contacting pad 66 of FIG. 6 (or any of the available contacting pads) could be formed to include a resistive element. As a non-limiting example, the resistive element could be provided in the form of a printed conductive ink. The thickness of the printed ink forming the resistive element, and resistivity of the ink composition, can be varied to achieve the desired resistance for a particular contacting pad. The additional information made available through this expansion of codes can include, but is not limited to, information related to hematocrit correction, information related to meter upgrades, and information related to the particular strip type. Accordingly, the use of such a resistive element can be used to expand the number of code configurations available with a set number of contacting pads.

It should be noted that the particular disclosed configurations of test strip 10, and in particular the configuration of connector contacts 38, 40 and the corresponding first and second plurality of electrical strip contacts, are merely exemplary, and different configurations could be formed without departing from the scope of the invention. For example, the underside of strip 10 can be formed to incorporate an additional number of contacting pads in order to increase the size (and thereby the amount of information) in the code index. The additional contacting pads on the underside of strip 10 could represent a third plurality of electrical strip contacts, thereby increasing the number of codes available. The number of available codes could thereby be expanded by applying an insulating coating to particular pads on the underside of strip 10 in addition to the coating of pads on the opposite side of the strip. Alternatively, all electrical strip contacts transmitting information from the measuring electrodes could be located on one side of the test strip and all electrical strip contacts related to information for presenting a code readable by a corresponding meter could be located on the opposite side of the test strip.

The incorporation of individualized code data within individual test strips provides numerous advantages in addition to those associated with accuracy of measurement. For example, with individual strip coding a user no longer needs to manually enter the meter's lot code, thereby removing the possibility of user error for this critical step. Strip lot codes stored directly on individual test strips will also provide a means to ship mixed lots of strips in a single strip vial. In contrast, current technologies such as button/key coding require all strips (typically packaged in a vial including 50 strips from the same lot) in a vial to be from the same lot code.

Individual strip coatings representing particular codes also afford bulk packaging benefits. For example, mixed lot test strips and vials including different numbers of strips will be possible. Strips from various lots could be stored in a central location and packaged for sale without the time and expense of strips are packaged from a single lot. Individual lot calibration codes stored on strips can also provide a means for varying a code across a single lot should a strip lot have variation from beginning to end or anywhere in between. Predetermined variations in manufacturing within a strip lot can be corrected by applying a continuously changing code across the lot, thereby solving yield problems and improving in-lot strip to strip variation. In addition, embedding lot codes on individual strips can be used to distinguish different types of test strips (e.g. glucose vs. ketone), check strips, or different manufacturing procedures, provide data for meter upgrades, and to correlate particular test strips for use only with a specific meter or meter type.

Figure 9A:
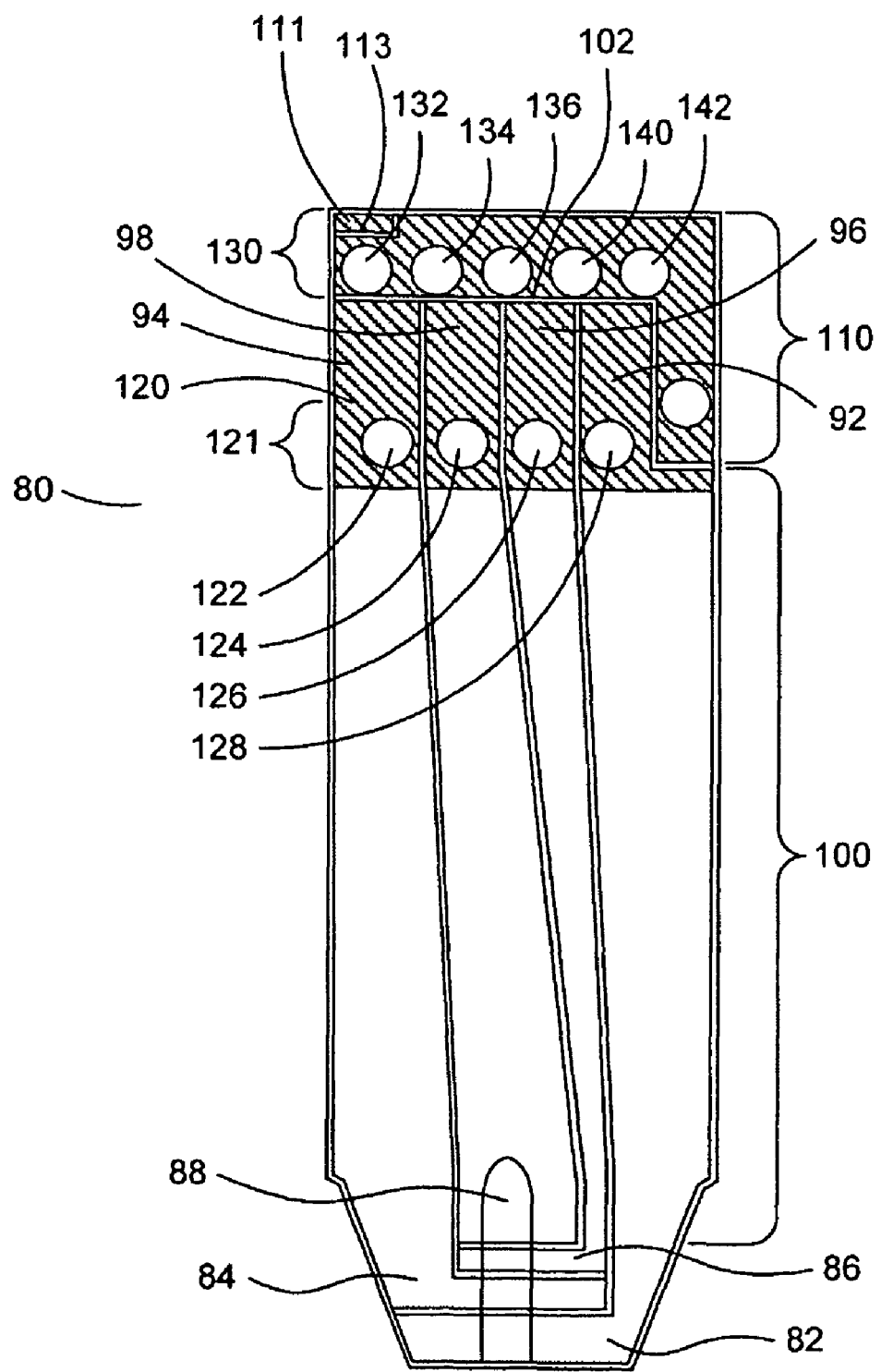
FIG. 9A is a top view of an alternative test strip illustrating an alternative configuration for providing a code.

FIG. 9A depicts a top view of a test strip 80 illustrating an alternative configuration for providing a code. As noted above, a test strip may include a conductive pattern provided over a base layer. The conductive pattern can be separated into distinct conductive regions forming different functional components of the test strip. In the embodiment of FIG. 9A, the conductive pattern may include a plurality of electrodes provided near a proximal end, a first and second conductive region provided near a distal end, and a plurality of conductive traces electrically connecting the electrodes to the first conductive region.

For example, the strip 80 may include a conductive pattern that forms a cathode electrode region 82, an anode electrode region 84, and first and second fill detect electrode regions 86 and 88 respectively, all of which are in contact with some portion of a sample cavity reception location 90. The four electrode regions 82, 84, 86, and 88, each lead to a corresponding conductive contact, 92, 94, 96, 98, for interfacing with a meter system. Accordingly, in the embodiment of FIG. 9A, a first conductive region 100 forms a plurality of electrical strip contacts 92-98. The first plurality of electrical strip contacts 92-98 are electrically connected to the plurality of measuring electrodes 82-88 at the distal end of the test strip 80. It should be understood that the four contacts 92-98 are merely exemplary, and the system could include fewer or more electrical strip contacts corresponding to the number of measuring electrodes included in the system.

As seen in FIG. 9A, a region of the strip 80 distal of the conductive region 100 forms a separate conductive region 110. Conductive region 110 is divided from conductive region 100, for example, through a break 102 formed through the underlying conductive pattern in the test strip 80. Break 102 could be formed in the conductive pattern during printing, through a scribe process, a micro-contact printing process, laser ablated, or through a chemical/photo-etching type process. In addition, other processes of forming conductive breaks by removing a conductor in the test strip 80 may be used as would be apparent to one having ordinary skill in the art. The particular conductive patterns illustrated are intended to be exemplary only, and alternative patterns, depending on the number of electrodes or the particular method of code presentation to the meter are contemplated. As seen in FIG. 9A, conductive region 110 may also include a rectangular sub-region 111 separated by a break 113. In embodiments including the sub-region 111, the conductive area inside region 111 presents a distinct contact pad that completes a wake-up circuit within the corresponding meter upon insertion.

The conductive pattern may be applied by providing a conductive material onto a base layer of the test strip 80 according to any known technique. For example, the conductive material may be provided by thin film vacuum sputtering of a conductive material (e.g. Gold) and a semiconductive material (e.g. Indium Zinc Oxide) onto a base layer. The resulting electrode layer can then by further patterned according to the specific application by forming particular conductive regions/pathways through a laser ablation process, or any of the methods listed above. Alternative materials and methods for providing a conductive pattern in addition to screen printing can be employed without departing from the scope of the invention.

Test strip 80 in FIG. 9A includes a layer of insulating material 120 overlaid onto the conductive regions 100 and 110. The insulating material 120 can be applied to the underlying test strip by virtue of an adhesive provided on an underside of the material 120, as will be described in more detail below. The insulating material is provided with a first plurality of apertures 121, comprised of apertures 122, 124, 126, and 128. The apertures 122-128 can be formed in the insulating material 120 prior to application of the material 120 over the conductive regions 100 and 110.

The first plurality of apertures 121 are arranged in the insulating material 120 in a configuration such that the apertures 122, 124, 126, and 128 overlay and expose the underlying electrical strip contacts 92, 94, 96, and 98, respectively. In addition, the insulating material 120 is provided with a second plurality of apertures 130, comprised of, for example, apertures 132, 134, 136, 138, 140, and 142. The second plurality of apertures 130 are arranged in the insulating material 120 in a configuration such that the apertures 132, 134, 136, 138, 140, and 142 overlay and expose the underlying conductive region 110.

Similar to the meter contact arrangement of FIG. 5, a specific meter strip connector (not shown) will be configured to accept the test strip 80. Upon final insertion of the test strip 80 into the corresponding meter, a first plurality of connector contacts in the meter will respectively engage (by virtue of the exposure provided by the first plurality of apertures 121) the underlying electrical strip contacts 92, 94, 96, and 98, thereby establishing an electrical connection path between the measuring electrodes 82-88 and the meter device. At the same time, a second plurality of meter contacts will either engage the underlying conductive region 110 or the insulating material 120, depending on the arrangement of the second plurality of 130.

Accordingly, expanding on the concept described above in FIGS. 4B and 6, for example, through operative connection of a predetermined number of contacts in the second plurality of meter contacts, the meter is presented with a particular code representing information signaling the meter to access data related to the underlying test strip 80. Similar to the non-conductive ink layer 75 (described in FIG. 6 above), the insulating material 120 provides a switching network to be read by the meter. When, upon final insertion of test strip 80 within a corresponding meter, material 120 covers a particular location beneath one of the second plurality of meter contacts, the insulating material 120 prevents the flow of electric current therealong and alters the conductive path along the second plurality of connector contacts (e.g. where no current flows through the particular meter contact engaged with the insulating material 120). When an aperture 130 is arranged to expose a particular portion of conductive region 110, current flow is relatively unimpeded (a low impedance path). Therefore, current flows through that particular meter contact (i.e., the meter contact engaged with region 110 by virtue of the aperture 130) in the second plurality of meter contacts and the resulting circuit characteristics are altered.

The resulting characteristics of the altered circuit present a particular code to the meter. An internal memory within the meter can then access, through a stored microprocessor algorithm, specific calibration information (such as, for example, calibration coefficients) relating to the particular test strip 80. The meter can read the code through either an analog or digital method as described above with regard to FIG. 7 or 8.

Figure 9B:
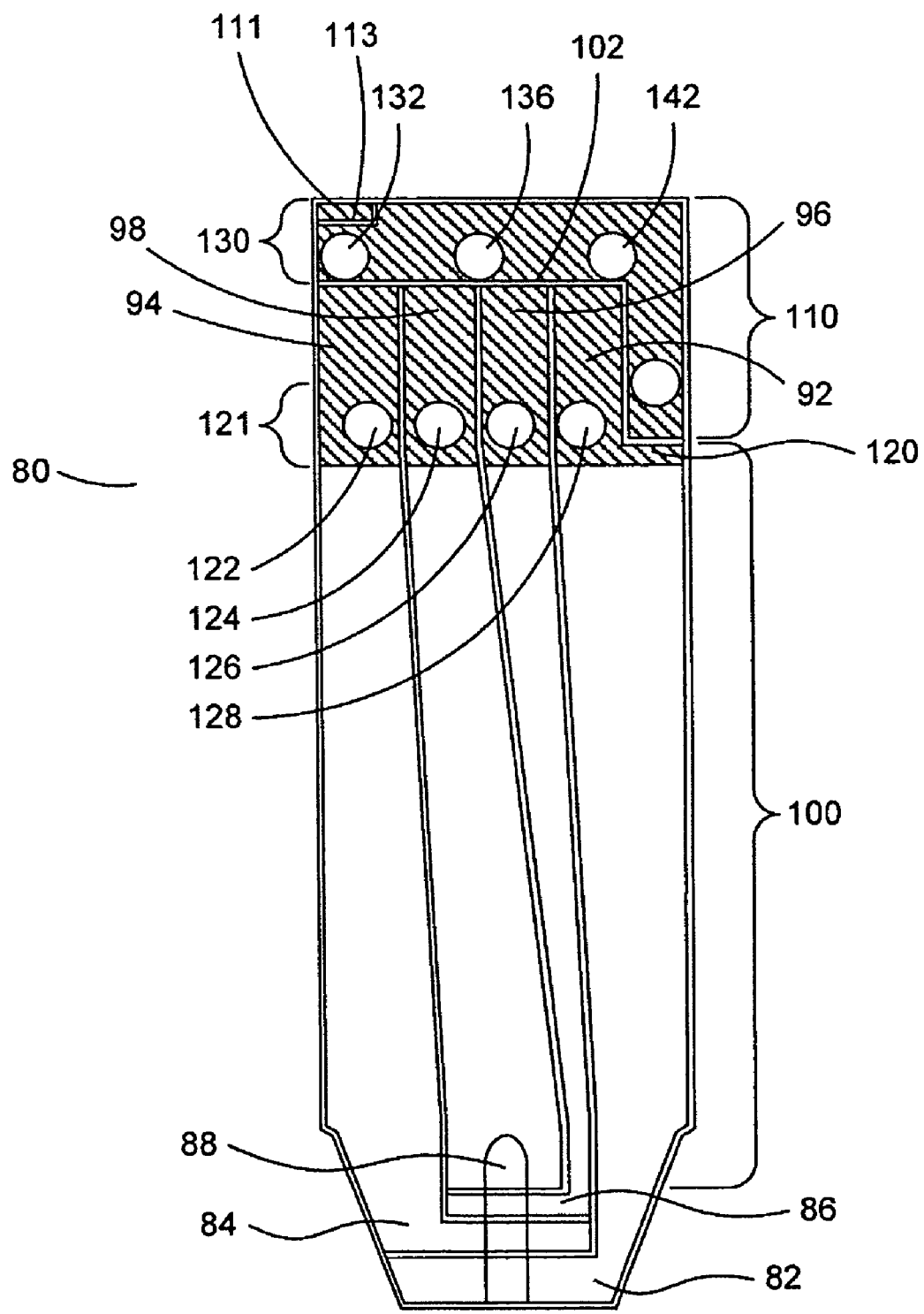
FIG. 9B is a top view of the test strip if FIG. 9A, illustrating an alternative code configuration.

The particular code presented to the second plurality of meter contacts can be altered by changing the particular pattern of apertures 130 provided in the insulating material 120. For example, in FIG. 9B, the test strip 80 is provided with an insulating material 120 presenting an aperture pattern different from that of FIG. 9A. More particularly, instead of five apertures 130 as illustrated in FIG. 9A, the insulating material of FIG. 9B presents 3 apertures, thereby only electrically exposing conductive region 110 to three corresponding contacts in the second plurality of meter contacts. Accordingly, the aperture pattern of FIG. 9B, causes altered circuit characteristics different from the circuit resulting from the pattern of FIG. 9A. This altered circuit of FIG. 9B, therefore, presents a different code to the meter than that presented by the configuration of FIG. 9A.

The system of providing a particular code pattern by virtue of an additional insulating material is advantageous for a number of reasons. For example, the particular aperture pattern can be formed in a separate layer of insulating material prior to application to the test strip 80. Such a procedure overcomes certain disadvantages prevalent in printing techniques where printing must be carefully controlled to assure that a particular insulating pattern does not interfere with a desired underlying conductive pattern. The use of an insulating material with a preformed aperture pattern and an adhesive backing provides a simple and efficient mechanism for repeatedly reproducing a particular code pattern on an underlying test strip. Once the aperture pattern is formed in the insulating material 120, the only further required step is applying the layer to the strip 80 by virtue of the adhesive backing.

The insulating material 120 may be comprised of a polymer film, such as, for example a PET (Polyethylene Terephthalate) material. It is preferred that the insulating material be able to flex with the biosensor substrate and resist wear or removal due to mechanical or thermal stress. Another preferred characteristic is the presentation of a relatively thin layer of insulation, thereby facilitating the formation of apertures via laser ablation or mechanical punching. For example, one exemplary material comprises MA370M PET film with a heat sealable ethylene acetate-based coating, available from 3M.

One advantage of the present application is provided due to the formation of apertures within the insulating material before it is applied to a test strip 80. The insulating material 120 can then be affixed to the test strip via adhesive 120. This adhesive may take a variety of forms with one preferred feature being the creation of a firm bond between the underlying test strip 80 and the insulating material 120. In addition, it is preferred that adhesive be presented such that it does not excessively exude from the underside of the insulating material and extend into the region of the apertures upon application. If the adhesive exudes and partially flows in the region of the aperture after application to the test strip 80, it may prevent conduction between the underlying conductive region and corresponding meter contact. Such blockage can erroneously present an incorrect code to the meter, resulting in serious clinical consequences.

Laser drilling is an exemplary technique that can be used to create the aperture pattern in the insulating material 120. A laser may be used to drill a prearranged pattern of holes into the insulating material 120, which can then be subsequently affixed to the substrate of the test strip 80, preferably in web form. An advantage of the laser is that it can draw patterns on the fly based on a computerized pattern. To change codes, one would simply prepare a new pattern in the laser's driver software. This obviates the need for tooling changes that are sometimes present in a mechanical system. The laser would avoid the accumulation of excess adhesive, as there is no need to physically touch the adhesive that may be present on the adhesive layer. It is also possible to compensate for pitch and edge variations, if the process is done on a reel to reel web format.

Another exemplary technique is using a punch press mechanism to stamp out a predetermined pattern into the insulator layer. One advantage of a punch process is the capability to stamp out many patterns at once. When using a mechanical punch press formation technique, it may be beneficial to use a heat seal adhesive for the insulating material 120 rather than pressure sensitive adhesives (PSAs) since PSAs can sometimes cause adhesive build-up in the punching tool over time.

With reference to FIG. 9A, another feature of the present application lies in the pattern and location of the first plurality of apertures 121 relative to the location of the second plurality of apertures 130. As seen in FIG. 9A, for example, the first plurality of apertures 121, exposing the strip contacts 92, 94, 96, and 98, are laterally staggered or offset from the second plurality of apertures 131, exposing predetermined portions of conductive region 110. Accordingly, similar to the staggered arrangement of FIG. 5 above, as a test strip 80 is inserted into a corresponding meter connector, the conductive path provided by conductive region 110 is unhindered by any scratches or scuffs that would otherwise result from first directly sliding the exposed portion of conductive region 110 under a non-staggered first plurality of meter connector contacts.

As a result of the staggered arrangement, during insertion, no portion of the conductive region 110 exposed by apertures 132-142 comes in contact with any of the meter connector contacts intended for final electrical connection with strip contacts 92-98. Accordingly, this staggered arrangement provides a more reliable electrical connection since there will be a reduced chance that the conductive coating from the conductive region 110 will be scratched and "plowed" away by the friction and interaction from the meter connector contacts.

Figure 10:
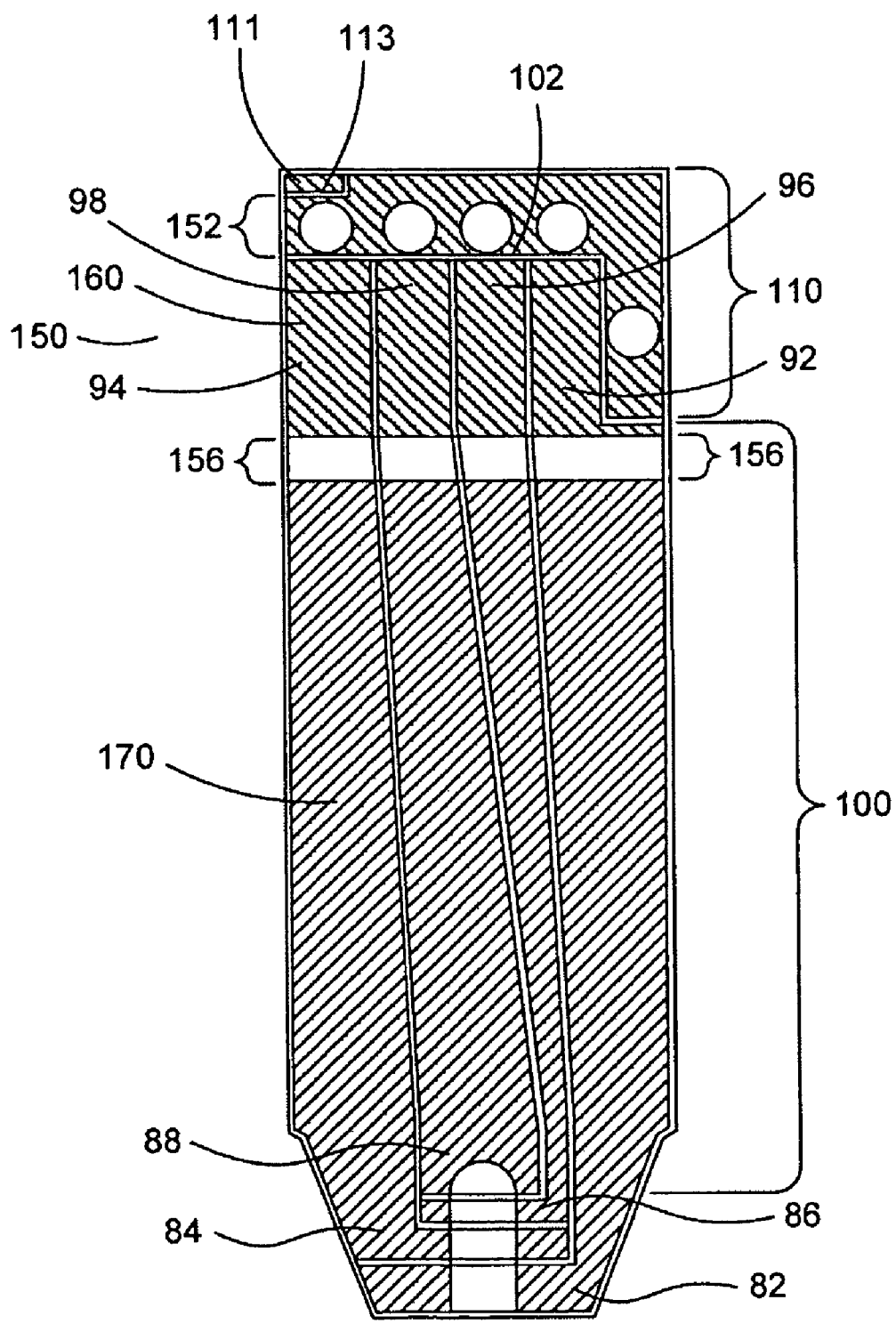
FIG. 10 is a top view of an alternative test strip providing a code.

FIG. 10 illustrates a top view of an alternative test strip providing a code. As seen in FIG. 10, a strip 150 is depicted. Just as in the embodiment of FIGS. 9A-9B, the strip 150 may include a conductive pattern that forms a conductive region 100 comprised of a cathode electrode region 82, an anode electrode region 84, and first and second fill detect electrode regions 86 and 88 respectively, all of which are in contact with some portion of a sample cavity reception location 90. The four electrode regions 80, 82, 84, and 88, each lead to a corresponding conductive contact, 92, 94, 96, 98, for interfacing with a meter system. Accordingly, a first conductive region 100 forms a plurality of electrical strip contacts 92-98. The first plurality of electrical strip contacts 92-98 are electrically connected to the plurality of measuring electrodes 82-88 at the distal end of the test strip 150.

A region of the strip 150 distal of the conductive region 100 forms a separate conductive region 110. Conductive region 110 is divided from conductive region 100, for example, through a break 102 formed through the underlying conductive pattern in the test strip 150. Accordingly, the underlying conductive pattern for strip 150 is the same as that provided for strip 80 described above. Test strip 150 includes an insulating material 160 having a different configuration than that described in FIG. 9A-9B. In FIG. 10, insulating material 160 includes only a single plurality of apertures 152. The plurality of apertures 152 presents a pre-determined arrangement of apertures, thereby exposing selective portions of the conductive region 110. Proximal of the area covered by the insulating material 160, the underlying conductive contacts, 92, 94, 96, and 98, are exposed for interfacing with a meter system. The test strip 150 may include an additional insulating material 170 provided over a proximal portion of the test strip. Due to the relative spacing between the distal insulating material 160 and the proximal insulating material 170, only a narrow portion 156 of conductive region 100 is exposed.

Upon final insertion of the test strip 150 into a corresponding meter, a first plurality of connector contacts in the meter will respectively engage the underlying electrical strip contacts 92, 94, 96, and 98, along the exposed narrow portion 156 proximal of the insulating material 160, thereby establishing an electrical connection path between the measuring electrodes 80-84 and the meter device. At the same time, the plurality of meter contacts will either engage the underlying conductive region 110 or the insulating material 120, depending on the arrangement of the plurality of apertures 152.

Figure 11:
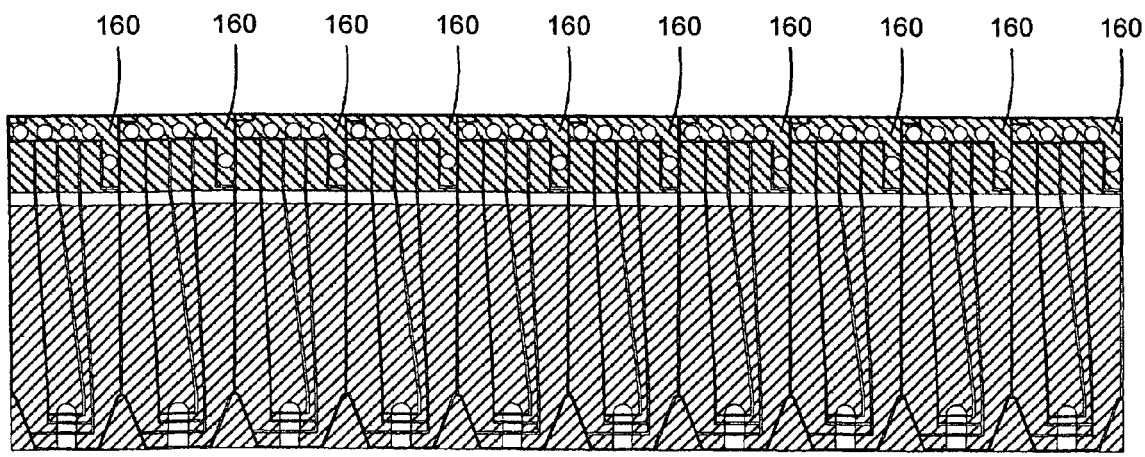
FIG. 11 is a top view of an array of test strips in the configuration of FIG. 10, each providing a code.

The arrangement of FIG. 10, therefore, provides a particular code arrangement for reception by a meter device, depending on the arrangement of apertures 152. In addition, the arrangement of FIG. 10 provides a cost benefit in that only a single group of apertures needs to be formed in the insulating material 160. This cost benefit can be further optimized by presenting a repeating pattern of insulating material 160 along a plurality of test strips. As seen in FIG. 11, insulating material 160, can be provided along a plurality of test strips. For example, a continuous web of insulating material having a particular pattern of apertures can be laid down via a continuous web technique, rather than discretely onto each sensor.

Figure 12:
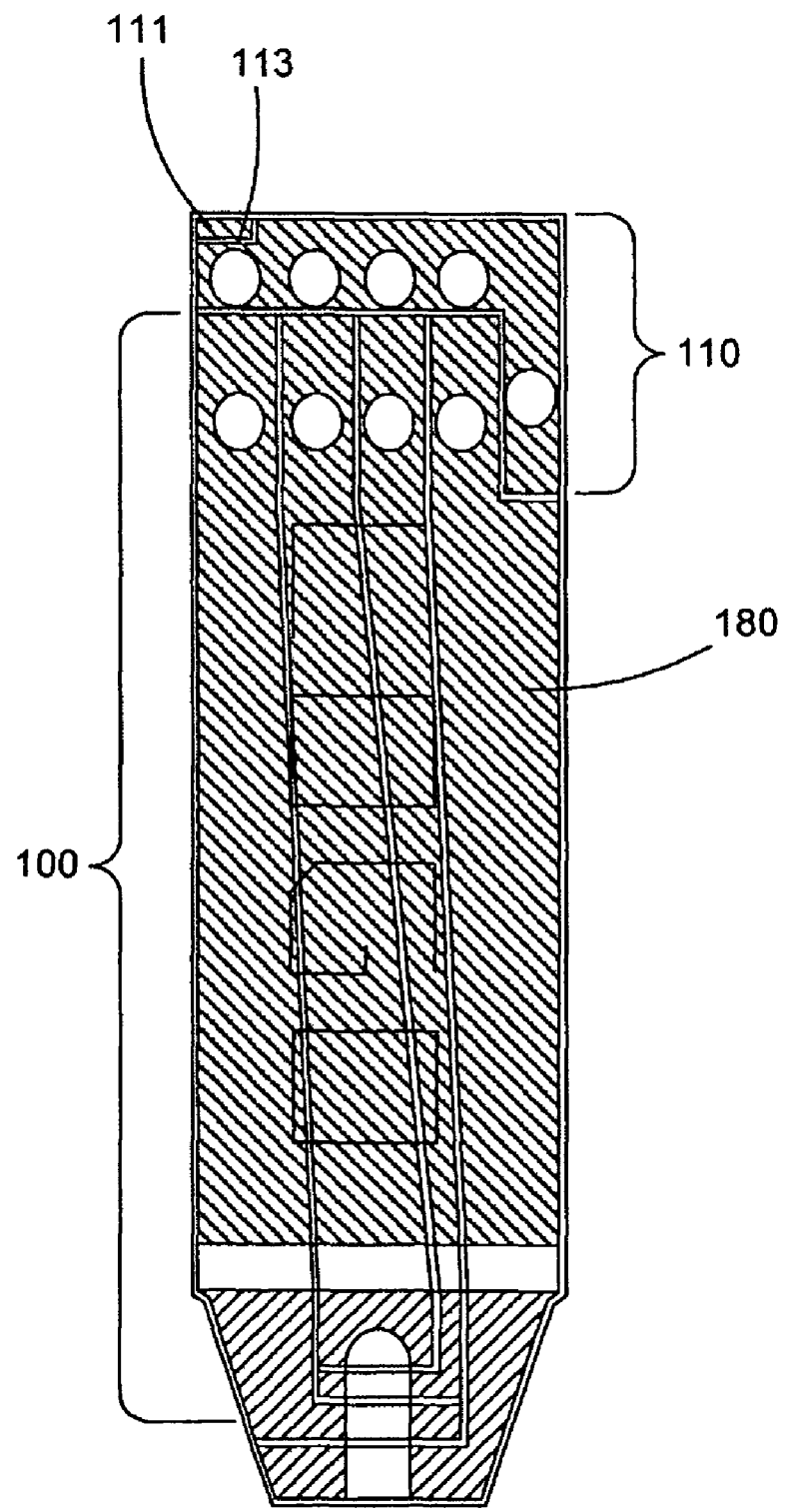
FIG. 12 is a top view of an alternative test strip providing a code and including informational indicia over a portion of the test strip.

FIG. 12 illustrates another arrangement for an insulating material for application along a test strip. As seen in FIG. 12, an insulating material 180 is applied to an underlying test strip. Similar to the embodiment of FIGS. 9A-9B, the insulating material includes a first and a second plurality of apertures, thereby exposing portions of conductive regions 100 and 110. In the example illustrated in FIG. 12, the insulating material 180 covers a relatively larger area of the test strip and may include informational indicia printed, or otherwise disposed thereon. Examples of informational indicia include, but are not limited to, a brand name or logo, patient information, testing instructions, indicia indicating insertion directions, and a website address.

Figure 13:
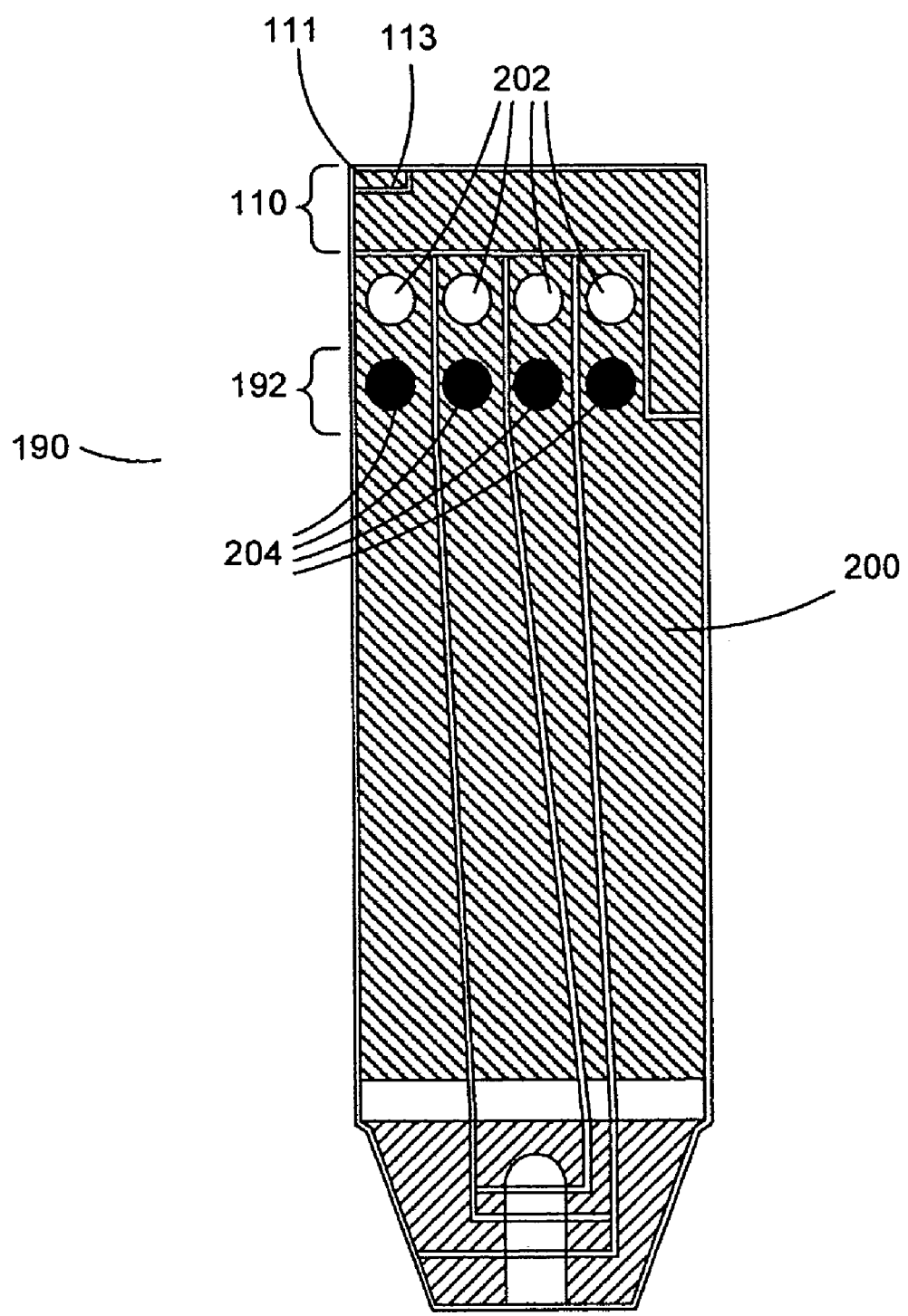
FIG. 13 is a top view of an alternative test strip illustrating an alternative configuration for providing a code.

FIG. 13 is a top view of an alternative test strip 190 illustrating an alternative system for providing a code. In the example of FIG. 13, the underlying test strip 190 includes a proximal plurality of apertures 192 that extend completely through the test strip 190. The test strip 190 also includes an insulating material 200 covering the underlying test strip 190. The insulating material 200 includes a first and a second plurality of apertures, the first plurality 202 exposing portions of conductive region 100 for presenting the measuring electrode signal to meter contacts, and the second set 204 arranged for alignment with the plurality of apertures 192 that extend completely through the test strip 190.

In the test strip system of FIG. 13, the proximal plurality of apertures 192 present a code readable by a corresponding test strip meter. The measurement electrodes are presented to and read by meter contacts through electrical conduction, just as in the previously described examples. The code presented by the plurality of apertures 192, however, is read by the corresponding meter based on a pattern of light transmitted through the test strip 190. A light source could be provided within the meter device configured to receive the test strip 190. The light source could be configured to present light along a path directed through the test strip such that pattern of light transmission through the test strip 190 depends on the pattern of apertures 192.

For example, a light source could be provided within the meter on one side of the test strip, while a light detector is arranged on another side of the meter, opposite the light source. Accordingly, depending on the pattern of apertures 192, a different amount, or pattern of light is received and detected by the light detector, resulting in a particular code being presented to the meter. One exemplary configuration may include an arrangement of photo-emitters in opposing relation to an arrangement of photo-detectors such that when one of apertures 192 is present, an associated photo-detector registers a "high", or binary "1" output. Conversely, where no aperture is present in a predetermined sensing location, an associated photo-detector registers a "low" or binary "0" output. Based on such a binary sensing system, a particular code can be presented and read by a properly configured test meter. The above described photo-detector and photo-emitter arrangement is intended to be one non-limiting example, and other arrangements are contemplated. For example, an alternative arrangement could read a code using only a single light source and a single light detector.

In the configuration of FIG. 13, the exposed portions of conductive region 100 are deliberately placed distal of the punched apertures 192. In this relative configuration, there is assurance that the meter contact pins configured for contacting conductive region 100 will avoid accidental engagement within the punched apertures 192. The approach of FIG. 12, does not require the use of conductive region 110 (which presents the code arrangement in other embodiments described above). FIG. 13 still depicts the region 110 being covered with a portion of the insulating material 200, however, since it may offer the advantage of protecting the conductive material in region 110 from being scribed, or "plowed" through, thus minimizing build-up of plowed conductive material in the connector.

FIG. 14A depicts an alternative test strip arrangement for presenting a code readable by a corresponding test strip meter. FIG. 14A illustrates the underside of a test strip 250. The measurement electrodes are located on the top surface (not shown) of the test strip 250 and are presented to, and read by, meter contacts through electrical conduction. For example, the measurement electrodes may be configured to connect with electrical strip contacts at the distal end of the top side of the test strip, which are in turn configured for reception by corresponding meter contacts, in a manner similar to that described in FIG. 9A above.

In the embodiment of FIG. 14A, a particular code is presented to a corresponding test meter by virtue of features located on the underside of the test strip 250. FIG. 14A depicts a covering 260 disposed over a distal portion of the underside of test strip 250. The covering 260 may be attached to the underside of the test strip 250 through an adhesive backing provided on the base (i.e., the underside) of the covering 260. Alternatively, the covering can be attached by glue or other similar methods.

The covering 260 is prepared to include discrete portions of electrically conductive indicia 270. For example, the covering 260 can be prepared to include conductive indicia 270 through the application of any conductive material on the covering 260. The conductive material forming indicia 270 may be applied by thin film vacuum sputtering through a mask of a conductive material (e.g. Gold), screen printing, ink jet printing, application of conductive ink, or any alternative process. As an alternative, a conductive pattern forming indicia 270 can be applied directly to the back of the back (i.e. underside) of the strip. In such an approach, since the indicia in provided directly on the base layer (e.g. a PET layer), covering 260 is not used.

In the arrangement of FIG. 14A, the conductive indicia 270 is comprised of four discrete regions of conductive material, 271-274 respectively. Each of the conductive regions 271-274 is configured for engagement with a corresponding meter contact to provide a switching network to be read by the meter. When, upon final insertion of test strip 250 within a corresponding meter, a predetermined meter contact location is covered by a discrete conductive region beneath one of a particular plurality of meter contacts, the conductive region (e.g., 271) allows for the flow of electric current therealong and alters the conductive path along the plurality of meter connector contacts (e.g. such that current flows through the particular meter contact engaged with the conductive region 271). When the conductive indicia 270 is arranged to align a particular meter contact with a region of the covering 260 that is absent any conductive material (such as region 275, for example), current flow is relatively impeded (a high impedance path). Therefore, little to no current flows through that particular meter contact (i.e., the meter contact engaged with an insulative top portion comprised of region 275) in the plurality of meter contacts and the resulting circuit characteristics are altered.

The resulting characteristics of the altered circuit thereby present a particular code to the meter. An internal memory within the meter can then access, through a stored microprocessor algorithm, specific calibration information (such as, for example, calibration coefficients) relating to the particular test strip 250. The meter can read the code through either an analog or digital method as described above with regard to FIG. 7 or 8.

FIG. 14B. illustrates another test strip 250 provided with an alternative arrangement for conductive indicia 270 on a covering 260. In the arrangement of FIG. 14B, the covering 260 includes an array of only three discrete conductive regions 281-283. The discrete conductive regions 281-283 are depicted as interspersed among two regions 284 and 285 of the covering 160 absent any conductive material. Due to this pattern, upon final insertion into a corresponding test meter, meter contacts that are configured for engagement with the regions 284 and 285 will not have current flow therethrough. As such, the circuit characteristics presented to the test meter will be altered. Accordingly, a different code from the one presented by the indicia arrangement of FIG. 14A is presented by the indicia arrangement of FIG. 14B.

The use of a covering 260 applied to an underside of a test strip is advantageous for a number of reasons. First, locating the meter contacts presenting a code to a test meter on a side opposite the side of the test strip that includes the electrode contacts, provides for more area on a single strip side to present a particular contact arrangement. For example, without the necessity to preserve space on a single side of the test strip, more area is available on either side for a predetermined meter function (e.g., presentation of electrode data or presentation of code data).

Second, providing a changeable pattern of conductive indicia 270 on a separately formed discrete covering 260, allows for cost savings and a plurality of options to be presented simply based on alteration of a conductive pattern formed on the covering 260. In addition, the use of a sticker-like adhesive material allows for the mass production of a series of code configurations that can be applied to a particular lot of strips at a later point in the manufacturing process, after the formation of an electrode conducting pattern. It is contemplated that the covering 260 having a conductive pattern of indicia 270 can be used to present a particular code readable by a test meter in any of the examples described above, not simply the two-sided embodiment of FIGS. 14A-14B. Additionally, while the covering 260 is illustrated as being provided at the distal end of the underside of the test strip 250, any other location on the underside of test strip 260 is contemplated (so long as engagement with corresponding meter contacts is allowed). Moreover, as an alternative to covering 260, a conductive pattern when we use a conductive ink on the back of the strip, we don't need the covering; we could print the ink directly on PET (slightly different implementation from what we have here).

In keeping with concepts described above, the covering 260 could be formed from a conductive material, such as metal foil, and the indicia 270 could be resistive, forming the coding pattern. Instead of indicia 270, openings such as punched holes in the conductive covering could provide non-conductive regions forming the coding patterns. In other words, the punched holes would enable contact between a particular meter contact and the underlying resistive (high impedance) area of the test strip base material.

Other embodiments of the invention will be apparent to those skilled in the art from consideration of the specification and practice of the invention disclosed herein. Unless disclosed otherwise, the particular features of every embodiment are intended to be combinable with, and may replace, or accompany, any of the features of any other embodiment described. It is intended that the specification and examples be considered as exemplary only, with a true scope and spirit of the invention being indicated by the following claims.

What is claimed is:

1. A method of making a test strip, said method comprising:
   providing a sample chamber;
   providing an electrically insulating base layer; and
   providing a conductive pattern formed on the base layer including a plurality of electrodes, a plurality of electrical strip contacts, conductive traces electrically connecting the electrodes to at least some of the electrical strip contacts, and a distinct distal conductive region provided distal to the electrical strip contacts;
   providing an electrically insulating material including a pattern of apertures; and
   disposing the electrically insulating material over at least a portion of the distal conductive region such that the apertures expose a pattern of the underlying distal conductive region to at least partially form a distinct machine-readable code representative of data particular to the test strip.

2. The method of claim 1, wherein providing the electrically insulating material comprises providing a PET (Polyethylene Terephthalate) material.

3. The method of claim 1, wherein the pattern of apertures are formed in the insulating material prior to disposing the electrically insulating material over at least a portion of the distal conductive region.

4. The method of claim 1, wherein the pattern of apertures are formed in the insulating material through a punching process.

5. The method of claim 1, wherein the pattern of apertures are formed in the insulating material through a laser ablation process.

6. A method of making a plurality of test strips, said method comprising:
   forming a plurality of test strip structures on one sheet, each of said test strip structures including:
      a sample chamber;
      an electrically insulating base layer; and
      a conductive pattern formed on said sheet including a plurality of electrodes, a plurality of electrical strip contacts, conductive traces electrically connecting the electrodes to at least some of the electrical strip contacts, and a distinct distal conductive region provided distal to the electrical strip contacts;
   providing an electrically insulating material including a pattern of apertures;
   disposing the electrically insulating material at least over a portion of the distal conductive region of each strip such that the apertures expose a pattern of the underlying distal conductive region on each strip to at least partially form a distinct machine-readable code representative of data particular to the test strip; and
   separating said test strip structures into said plurality of test strips.

7. The method of claim 6, wherein providing the electrically insulating material comprises providing a PET (Polyethylene Terephthalate) material.

8. The method of claim 6, wherein the pattern of apertures are formed in the insulating material prior to disposing the electrically insulating material over at least a portion of the distal conductive region.

9. The method of claim 6, wherein the pattern of apertures are formed in the insulating material through a punching process.

10. The method of claim 6, wherein the pattern of apertures are formed in the insulating material through a laser ablation process.

11. The method of claim 6, wherein the electrically insulating material is disposed over the test strips as a continuous web of material.

* * * * *